United States Patent
Leonard et al.

(10) Patent No.: US 7,405,207 B2
(45) Date of Patent: Jul. 29, 2008

(54) NEBULIZER FORMULATIONS OF DEHYDROEPIANDROSTERONE AND METHODS OF TREATING ASTHMA OR CHRONIC OBSTRUCTIVE PULMONARY DISEASE USING COMPOSITIONS THEREOF

(75) Inventors: Sherry A. Leonard, Lawrenceville, NJ (US); Keith A. Johnson, Durham, NC (US)

(73) Assignee: Epigenesis Pharmaceuticals, Inc., Cranbury, NJ (US)

( * ) Notice: Subject to any disclaimer, the term of this patent is extended or adjusted under 35 U.S.C. 154(b) by 714 days.

(21) Appl. No.: 10/462,901

(22) Filed: Jun. 17, 2003

(65) Prior Publication Data

US 2004/0067920 A1    Apr. 8, 2004

Related U.S. Application Data

(60) Provisional application No. 60/389,242, filed on Jun. 17, 2002.

(51) Int. Cl.
*A61K 31/56* (2006.01)
*A61K 31/566* (2006.01)
*A61K 31/568* (2006.01)
*A61K 31/5685* (2006.01)
*C07J 69/00* (2006.01)

(52) U.S. Cl. .................. 514/173; 424/46; 424/489; 540/2; 540/7

(58) Field of Classification Search .............. None
See application file for complete search history.

(56) References Cited

U.S. PATENT DOCUMENTS

| | | | |
|---|---|---|---|
| 3,943,987 A * | 3/1976 | Rossi ................. | 206/524.8 |
| 4,379,842 A | 4/1983 | Fujiwara et al. | |
| 4,393,066 A | 7/1983 | Garrett et al. | |
| 4,499,064 A | 2/1985 | Shive | |
| 4,518,595 A | 5/1985 | Coleman et al. | |
| 4,575,498 A | 3/1986 | Holmes et al. | |
| 4,628,052 A | 12/1986 | Peat | |
| 4,789,669 A | 12/1988 | Sugimoto et al. | |
| 4,920,115 A | 4/1990 | Nestler et al. | |
| 4,931,441 A | 6/1990 | Lawrence | |
| 4,985,443 A | 1/1991 | Montes | |
| 5,021,417 A | 6/1991 | Prost | |
| 5,059,595 A | 10/1991 | Le Grazie | |
| 5,077,284 A | 12/1991 | Loria et al. | |
| 5,110,810 A | 5/1992 | Eich et al. | |
| 5,118,505 A | 6/1992 | Költringer | |
| 5,162,198 A | 11/1992 | Eich et al. | |
| 5,173,488 A | 12/1992 | Haeger | |
| 5,177,076 A | 1/1993 | Nijkerk et al. | |
| 5,266,312 A | 11/1993 | Leung et al. | |
| 5,270,305 A | 12/1993 | Palmer | |
| 5,347,005 A | 9/1994 | Mueller et al. | |
| 5,407,684 A | 4/1995 | Loria et al. | |
| 5,407,927 A | 4/1995 | Morales et al. | |
| 5,489,581 A | 2/1996 | Daynes et al. | |
| 5,527,789 A | 6/1996 | Nyce | |
| 5,532,230 A | 7/1996 | Daynes et al. | |
| 5,538,734 A | 7/1996 | Le Grazie | |
| 5,583,126 A | 12/1996 | Daynes et al. | |
| 5,635,496 A | 6/1997 | Daynes et al. | |
| 5,686,438 A | 11/1997 | Daynes et al. | |
| 5,703,063 A | 12/1997 | Chasalow et al. | |
| 5,767,278 A | 6/1998 | Gaeta et al. | |
| 5,811,418 A | 9/1998 | Daynes et al. | |
| 5,859,000 A | 1/1999 | Dowell et al. | |
| 5,861,391 A | 1/1999 | Yen et al. | |
| 5,948,434 A | 9/1999 | Labrie | |
| 6,093,706 A | 7/2000 | Zeligs | |
| 2002/0032160 A1 * | 3/2002 | Nyce .................. | 514/26 |
| 2002/0042401 A1 | 4/2002 | Ferguson et al. | |
| 2003/0013772 A1 | 1/2003 | Murphy et al. | |
| 2003/0138434 A1 | 7/2003 | Campbell et al. | |
| 2003/0139331 A1 | 7/2003 | Martin et al. | |

(Continued)

FOREIGN PATENT DOCUMENTS

WO    WO 00/54763    7/2000

(Continued)

OTHER PUBLICATIONS

Araneo et al., "Dehydroepiandrosterone Reduces Progressive Dermal Ishemia Caused by Thermal Injury," *J. Surg. Res.* 59(2):250-62 (1995).
Bonnett et al., "Dehydroepiandrosteron (DHEA) prevents and reverses chronic hypoxic pulmonary hypertension," *PNAS* 100(16):9488-93 (2003).
Budavari, The Merck Index 11th ed., 1989, pp. 660-661, monograph 4141.
Coleridge et al., "Intravenous aminophylline confers no benefit in acute asthma treated with intravenous steroids and inhaled bronchodilators", *Aust. N.Z. J. Med.* 23:348-54 (1993).
Dashtaki et al., "Dehydroepiandrosterone and Analogs Inhibit DNA Binding of AP-1 and Airways Smooth Muscle Proliferation," *J. Pharmacol. EXD. Thera.* 285(2):876-83 (1998).

(Continued)

*Primary Examiner*—Johann Richter
*Assistant Examiner*—James H Alstrum Acevedo
(74) *Attorney, Agent, or Firm*—Albert P. Halluin; Robert H. Reamey; Wilson Sonsini Goodrich & Rosati

(57) ABSTRACT

This invention relates to a sealed container containing a powder formulation comprising a dehydroepiandrosterone, its analogue(s) or salt(s) by itself or with a pharmaceutically or veterinarily acceptable carrier or diluent, and having a particle size of about 0.1 μm to about 100 μm. The formulation can be used to treat or prevent asthma, chronic obstructive pulmonary disease, lung inflammation, and other respiratory diseases or conditions. The formulation may be prepared by jet milling, and may be delivered through the respiratory tract or other routes using a nebulizer. The sealed container is provided in a device and/or a therapeutic kit.

21 Claims, 7 Drawing Sheets

U.S. PATENT DOCUMENTS

Figure 1:
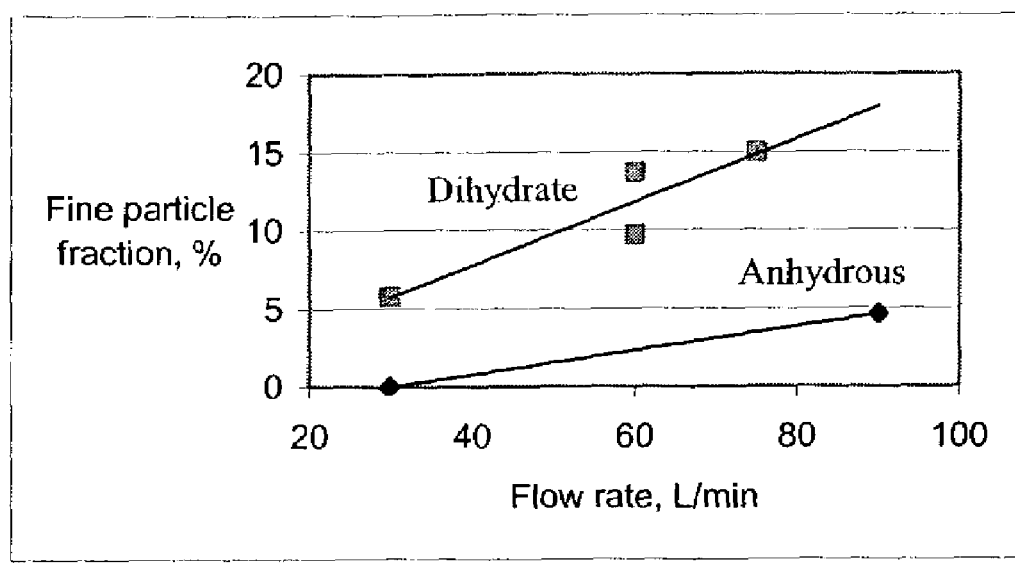

2003/0216329 A1    11/2003    Robinson et al.

FOREIGN PATENT DOCUMENTS

| WO | WO 01/015745 | 7/2000 |
| WO | WO 02/069955 | 7/2000 |
| WO | WO 03/072572 | 7/2000 |
| WO | WO 93/16704 | 7/2000 |
| WO | WO 96/16680 | 7/2000 |
| WO | WO 97/48367 | 7/2000 |
| WO | WO 98/03180 | 7/2000 |

OTHER PUBLICATIONS

Dompeling et al., "Treatment with Inhaled Steroids in Asthma and Chronic Bronchitis Long Term Compliance and Inhaler Technique", *Family Practice* 9(2):161-6 (1992).

Dunn, et al., "Dehydroepiandrosterone sulphate concentrations in asthmatic patients: pilot study," *N.Z. J. Med.* 97(768):805-8 (1984).

Dworksi et al., "Conspectus: Inhaled Steroids in Asthma", *Comprehensive Therapy*, 18,3 (1992).

Fehér et al., "Adrenocortical Function in Bronchial Asthma", *Acta Medica Hungarica* 40(2-3):125-32 (1983).

Fehér, et al., "Dehydroepiandrosterone Therapy of Patients with Corticosteroid Dependent Bronchial Asthma," *Natl. Institute of Rheumatism and Physiotherapy*, in XIII Congress of the European Academy of Allergology and Clinical Immunology, eds. (Saba, et al., Debrecen Hungary (1986).

Hampl et al., "Dehydroepiandrosterone sulphate reduces chronic hypoxic pulmonary hypertensions in rats," *J. Eur. Respir*, 21:862-5 (2003).

Holzmann et al., "Therapy of Psoriasis with Dehydroepiandrosterone-Enanthate. II. Intramuscular Depot Application of 300 mg", *Arch. Dermatol. Forsch.* 247(1):23-8 (1973) (German with English Abstract).

Hummel et al., "Comparison of oral-steroids sparing by high-dose and low-dose inhaled steroid in maintenance treatment of severe asthma", *The Lancet*, 340(8834/8835):1483-7 (1992).

Ishihara et al., "Gas Chromatographic Determination of Degradation Products and Stability of Dehydroepiandrosterone Sulfate in Aqueous Solution," *Drug Development and Industrial Pharmacy*. 1979; 5(9): 263-275.

Itagaki et al., "Effect of Cortisol on the Release of Human Decidual", Caplus, 114875 (1991) (Japanese with English Abstract).

Koó et al., "Our experiences with Dehydroepiandrosterone Therapy in Steroid-Dependent Intrinsic Bronchical Asthma", *Orvosi Hetilap* 128(38):1995-7 (1987) (English translation).

Lejeune, "Pathogenesis of Mental Impairment in Tristomy 21", *Annales de Genetique*, 34(2): 55-64 (1991) (French with English Abstract).

Mileva et al., "Andostenedione, DHEA sulfact, cortisol, aldosterone and testosterone in asthmatic patients", 07608054 (1990) (Russian with English Abstract).

Nakagawa, et al., The Properties of Water of Crystallization of Sodium Prasterone Sulfate, *Chem. Pharm. Bull* 29(5): 1466-9 (1981).

Nakagawa, et al., "The of Grinding and Drying on the Solid State Stability of Sodium Prasterone Sulfate," *Chem. Pharm. Bull* 30(1):242-8 (1982).

Pashko et al., "Inhibition of 7,12-dimethylbenz(a)anthracene-induced Skin Papillomas and Carcinomas by Dephydroepiandrosterone and 3-beta-methylandrost-5-en-17-one in mice", *Cancer Res.* 45(1):164-6 (1985).

Peeters et al., "Differences in Purine Metabolism in Patients with Down's Syndrome", *J. Intellect. Diabil. Res.* 37:471 (1993). Abstract.

Reed, "Aerosol Steroids as Primary Treatment of Mild Asthma", *New England J. Med.* 325(6):425-6 (1991).

Rowe et al., "Effectiveness of Steroid Therapy in Acut Exacerbations of Asthma: A Meta-analysis", *Amer. J. Emergency Med.* 10(4):301-10 (1992).

Sasaki et al., "Cervical Ripening with Dehydroepiandrosterone Sulphate", *Br. J. Obstet. Gynaecol.* 89(3):195-8, (1982).

Sciarra et al., "Aerosols", *Remington's Pharmaceutical Sciences*, $18^{th}$ ed. (1990), Eds. Gennaro et al., pp. 1873-1875 and 1694-1712.

Sharma et al., "Screening of potential chemopreventive agents using biochemical markers of carcinogenesis", *Cancer Res.* 54(22):5848-55 (1994).

Shomali, "The Use of Anti-Aging Hormones Melatonin. Growth Hormone, Testosterone, and Dehydroepiandrosterone: Consumer Enthusiam for Unproven Therapies", *Md. Med. J.* 46(4):181-6 (1997).

Sonka et al., "Gout and Dehydroepiandrosterone: 3. DHEA Administration", *Endokrynologia Polska* 24(3):209-18 (1973).

Sur et al., "Double-blind trial pyroxidine (vitamin B6) in the treatment of steroid-dependent asthma", *Ann. Allergy*. 70:147-52 (1993).

Schwartz et al., "Inhibition of 7,12-dimethylbenz[a]anthracene- and urethan-induced lung tumor formation in A/J mice by long-term treatment with dehvdroepiandrosterone," *Carcinoaenesis* 2(12):1335-7 (1981).

Van de Graaf et al., "Respiratory Membrane Permeability and Bronchial Hyperreactivity in Patients with Stable Asthma: Effects of Therapy with Inhaled Steroids", *Bronchial Asthma and Respiratory Membrane Permeability* 143:362-8 (1991).

Van Vollenhoven et al., "Dehydroepiandrosterone in SLE. Results of a Double-Blind, Placebo-Controlled, Randomized Clinical Trial." *Arthritis Rheum*. 38(12): 1826-31 (1995).

Wolkowitz et al., "Dehydroepiandrosterone Treatment of Depression", *Biol. Psychiatry* 41 (3):311-8. (1997).

Ma, Y. Synthesis of Prasterone Sulfate Sodium Dihydrate. Academic Journal of Guangdong College of Pharmacy. 2000; 15(3):181-182. (in Chinese with English abstract).

\* cited by examiner

NEBULIZER FORMULATIONS OF DEHYDROEPIANDROSTERONE AND METHODS OF TREATING ASTHMA OR CHRONIC OBSTRUCTIVE PULMONARY DISEASE USING COMPOSITIONS THEREOF

This application is a non-provisional application that claims priority to the U.S. Provisional Patent Application Ser. No. 60/389,242, filed Jun. 17, 2002; and is a non-provisional application that claims priority to the U.S. Provisional Patent Application 60/477,987, filed Jun. 11, 2003.

BACKGROUND OF THE INVENTION

1. Field of the Invention

This invention relates to a respirable dry powder formulation comprising a pharmaceutically or veterinarily acceptable carrier and a dehydroepiandrosterone (DHEA), DHEA derivative, or pharmaceutically or veterinarily acceptable salt thereof, sealed in a nebulizable form. Methods for preparation and delivering of the dry powdered formulation, and for treating asthma, chronic obstructive pulmonary disease (COPD), or other respiratory disease or condition, including microbial (including bacteria) or viral caused respiratory disease, such as severe acute respiratory syndrome (SARS). The formulation is provided in the form of a kit.

2. Description of the Background

Asthma and COPD and other respiratory ailments, associated with a variety of diseases and conditions, are extremely common in the general population, and more so in certain ethnic groups, such as African Americans. Respiratory ailments include microbial infections or viral infections (such as SARS). In many cases they are accompanied by inflammation, which aggravates the condition of the lungs. Asthma, for example, is one of the most common diseases in industrialized countries. In the United States it accounts for about 1% of all health care costs. An alarming increase in both the prevalence and mortality of asthma over the past decade has been reported, and asthma is predicted to be the preeminent occupational lung disease in the next decade. While the increasing mortality of asthma in industrialized countries could be attributable to the reliance upon beta agonists in the treatment of this disease, the underlying causes of asthma remain poorly understood.

Asthma is a condition characterized by variable, in many instances reversible obstruction of the airways. This process is associated with lung inflammation and in some cases lung allergies. Many patients have acute episodes referred to as "asthma attacks," while others are afflicted with a chronic condition. The asthmatic process is believed to be triggered in some cases by inhalation of antigens by hypersensitive subjects. This condition is generally referred to as "extrinsic asthma." Other asthmatics have an intrinsic predisposition to the condition, which is thus referred to as "intrinsic asthma," and may be comprised of conditions of different origin, including those mediated by the adenosine receptor(s), allergic conditions mediated by an immune IgE-mediated response, and others. All asthmas have a group of symptoms, which are characteristic of this condition: bronchoconstriction, lung inflammation and decreased lung surfactant. Existing bronchodilators and anti-inflammatories are currently commercially available and are prescribed for the treatment of asthma. The most common anti-inflammatories, corticosteroids, have considerable side effects but are commonly prescribed nevertheless. Most of the drugs available for the treatment of asthma are, more importantly, barely effective in a small number of patients.

Chronic obstructive pulmonary disease (COPD) causes a continuing obstruction of airflow in the airways. COPD is characterized by airflow obstruction that is generally caused by chronic bronchitis, emphysema, or both. Commonly, the airway obstruction is mostly irreversible. In chronic bronchitis, airway obstruction results from chronic and excessive secretion of abnormal airway mucus, inflammation, bronchospasm, and infection. Chronic bronchitis is also characterized by chronic cough, mucus production, or both, for at least three months in at least two successive years where other causes of chronic cough have been excluded. In emphysema, a structural element (elastin) in the terminal bronchioles is destroyed leading to the collapse of the airway walls and inability to exhale "stale" air. In emphysema there is permanent destruction of the alveoli. Emphysema is characterized by abnormal permanent enlargement of the air spaces distal to the terminal bronchioles, accompanied by destruction of their walls and without obvious fibrosis. COPD can also give rise to secondary pulmonary hypertension. Secondary pulmonary hypertension itself is a disorder in which blood pressure in the pulmonary arteries is abnormally high. In severe cases, the right side of the heart must work harder than usual to pump blood against the high pressure. If this continues for a long period, the right heart enlarges and functions poorly, and fluid collects in the ankles (edema) and belly. Eventually the left heart begins to fail. Heart failure caused by pulmonary disease is called cor pulmonale.

COPD characteristically affects middle aged and elderly people, and is one of the leading causes of morbidity and mortality worldwide. In the United States it affects about 14 million people and is the fourth leading cause of death, and the third leading cause for disability in the United States. Both morbidity and mortality, however, are rising. The estimated prevalence of this disease in the United States has risen by 41% since 1982, and age adjusted death rates rose by 71% between 1966 and 1985. This contrasts with the decline over the same period in age-adjusted mortality from all causes (which fell by 22%), and from cardiovascular diseases (which fell by 45%). In 1998 COPD accounted for 112,584 deaths in the United States.

COPD, however, is preventable, since it is believed that its main cause is exposure to cigarette smoke. Long-term smoking is the most frequent cause of COPD. It accounts for 80 to 90% of all cases. A smoker is 10 times more likely than a non-smoker to die of COPD. The disease is rare in lifetime non-smokers, in whom exposure to environmental tobacco smoke will explain at least some of the airways obstruction. Other proposed etiological factors include airway hyper responsiveness or hypersensitivity, ambient air pollution, and allergy. The airflow obstruction in COPD is usually progressive in people who continue to smoke. This results in early disability and shortened survival time. Stopping smoking reverts the decline in lung function to values for non-smokers. Other risk factors include: heredity, second-hand smoke, exposure to air pollution at work and in the environment, and a history of childhood respiratory infections. The symptoms of COPD include: chronic coughing, chest tightness, shortness of breath, an increased effort to breathe, increased mucus production, and frequent clearing of the throat.

There is very little currently available to alleviate symptoms of COPD, prevent exacerbations, preserve optimal lung function, and improve daily living activities and quality of life. Many patients will use medication chronically for the rest of their lives, with the need for increased doses and additional drugs during exacerbations. Medications that are currently prescribed for COPD patients include: fast-acting $\beta$2-agonists, anticholinergic bronchodilators, long-acting bronchodilators, antibiotics, and expectorants. Amongst the currently available treatments for COPD, short term benefits, but not long term effects, were found on its progression, from administration of anti-cholinergic drugs, β2 adrenergic agonists, and oral steroids.

Short and long acting inhaled β2 adrenergic agonists achieve short-term bronchodilation and provide some symptomatic relief in COPD patients, but show no meaningful maintenance effect on the progression of the disease. Short acting β2 adrenergic agonists improve symptoms in subjects with COPD, such as increasing exercise capacity and produce some degree of bronchodilation, and even an increase in lung function in some severe cases. The maximum effectiveness of the newer long acting inhaled, β2 adrenergic agonists was found to be comparable to that of short acting β2 adrenergic agonists. Salmeterol was found to improve symptoms and quality of life, although only producing modest or no change in lung function. In asthmatics, however, β2 adrenergic agonists have been linked to an increased risk of death, worsened control of asthma, and deterioration in lung function. β2-agonists, such as albuterol, help to open narrowed airways. The use of β2-agonists can produce paradoxical bronchospasm, which may be life threatening to the COPD patient. In addition, the use of β2-agonists can produce cardiovascular effects, such as altered pulse rate, blood pressure and electrocardiogram results. In rare cases, the use of β2-agonists can produce hypersensitivity reactions, such as urticaria, angioedema, rash and oropharyngeal edema. In these cases, the use of the β2-agonist should be discontinued. Continuous treatment of asthmatic and COPD patients with the bronchodilators ipratropium bromide or fenoterol resulted in a faster decline in lung function, when compared with treatment provided on a need basis, therefore indicating that they are not suitable for maintenance treatment. The most common immediate adverse effect of β2 adrenergic agonists, on the other hand, is tremors, which at high doses may cause a fall in plasma potassium, dysrhythmias, and reduced arterial oxygen tension. The combination of a β2 adrenergic agonist with an anti-cholinergic drug provides little additional bronchodilation compared with either drug alone. The addition of ipratropium to a standard dose of inhaled β2 adrenergic agonists for about 90 days, however, produces some improvement in stable COPD patients over either drug alone. Anticholinergic agents were found to produce greater bronchodilation in combination with anti-cholinergic agents than β2 adrenergic agonists, in people with COPD. Overall, the occurrence of adverse effects with β2 adrenergic agonists, such as tremor and dysrhythmias, is more frequent than with anti-cholinergics. Thus, neither anti-cholinergic drugs nor β2 adrenergic agonists have an effect on all people with COPD; nor do the two agents combined.

Anti-cholinergic drugs achieve short-term bronchodilation and produce some symptom relief in people with COPD, but no improved long-term prognosis even with inhaled products. Most COPD patients have at least some measure of airways obstruction that is somewhat alleviated by ipratropium bromide. "The lung health study" found in men and women smokers spirometric signs of early COPD. Three treatments compared over a five year period found that ipratropium bromide had no significant effect on the decline in the functional effective volume of the patient's lungs whereas smoking cessation produced a slowing of the decline in the functional effective volume of the lungs. Ipratropium bromide, however, produced serious adverse effects, such as cardiac symptoms, hypertension, skin rashes, and urinary retention. Anticholinergic bronchodilators, such as ipratropium bromide, and theophylline derivatives, help to open narrowed airways. Long-acting bronchodilators help to relieve constriction of the airways and help prevent bronchospasm associated with COPD. Theophyllines have a small bronchodilatory effect in COPD patients whereas they have some common adverse effects, and they have a small therapeutic range given that blood concentrations of 15-20 mg/l are required for optimal effects. Adverse effects include nausea, diarrhea, headache, irritability, seizures, and cardiac arrhythmias, and they occur at highly variable blood concentrations and, in many people, they occur within the therapeutic range. The theophyllines' doses must be adjusted individually according to smoking habits, infection, and other treatments, which is cumbersome. Although theophyllines have been claimed to have an anti-inflammatory effect in asthma, especially at lower doses, none has been reported in COPD, although their bronchodilating short-term effect appears to be statistically different from placebo. The adverse effects of theophyllines and the need for frequent monitoring limit their usefulness. There is no evidence that anti-cholinergic agents affect the decline in lung function, and mucolytics have been shown to reduce the frequency of exacerbations but with a possible deleterious effect on lung function. The long-term effects of β2 adrenergic agonists, oral corticosteroids, and antibiotics have not yet been evaluated, and up to the present time no other drug has been shown to affect the progression of the disease or survival.

Oral corticosteroids elicit some improvement in baseline functional effective volume in stable COPD patients whereas systemic corticosteroids have been found to be harmful at least producing some osteoporosis and inducing overt diabetes. The longer term administration of oral corticosteroids may be useful in COPD, but their usefulness must be weighed against their substantial adverse effects. Inhaled corticosteroids have been found to have no real short-term effect on airway hyper-responsiveness to histamine, but a small long-term effect on lung function, e.g., in pre-bronchodilator functional effective volume. Fluticasone treatment of COPD patients showed a significant reduction in moderate and severe (but not mild) exacerbations, and a small but significant improvement in lung function and six minute walking distance. Oral prednisolone, inhaled beclomethasone or both had no effects in COPD patients, but lung function improved oral corticosteroids. Mucolytics have a modest beneficial effect on the frequency and duration of exacerbations but an adverse effect on lung function. Neither N-acetylcysteine nor other mucolytics, however, have a significant effect in people with severe COPD (functional effective volume<50%) in spite of evidencing greater reductions in frequency of exacerbation. N-acetylcysteine produced gastrointestinal side effect. Long-term oxygen therapy administered to hypoxaemic COPD and congestive cardiac failure, patients, had little effect on their rates of death for the first 500 days or so, but survival rates in men increased afterwards and remained constant over the next five years. In women, however, oxygen decreased the rates of death throughout the study. Continuous oxygen treatment of hypoxemic COPD patients (functional effective volume<70% predicted) for 19.3 years decreased overall risk of death. To date, however, only life style changes, smoking cessation and long term treatment with oxygen (in hypoxaemics), have been found to alter the long-term course of COPD.

Antibiotics are also often given at the first sign of a respiratory infection to prevent further damage and infection in diseased lungs. Expectorants help loosen and expel mucus secretions from the airways, and may help make breathing easier.

In addition, other medications may be prescribed to manage conditions associated with COPD. These may include: diuretics (which are given as therapy to avoid excess water retention associated with right-heart failure), digitalis (which strengthens the force of the heartbeat), painkillers cough suppressants, and sleeping pills. This latter list of medications help alleviate symptoms associated with COPD but do not treat COPD.

Thus, there is very little currently available to alleviate symptoms of COPD, prevent exacerbations, preserve optimal lung function, and improve daily living activities and quality of life.

Severe acute respiratory syndrome (SARS) is a respiratory illness that has recently been reported in Asia, North America, and Europe. In general, SARS patients initial experience a fever of greater than 100.4° F. (>38.0° C.). This may be accompanied or followed by headache, an overall feeling of discomfort, and body aches. Certain patients also experience respiratory symptoms. Following 2 to 7 days, SARS patients may also develop a dry cough and experience breathing trouble. SARS appears to spread primarily by close person-to-person contact. The majority of SARS patients appear to have been involved people who cared for or lived with others with SARS, or had direct contact with an infectious material (e.g., respiratory secretions) from another patient with SARS. Potential ways in which SARS can be spread include touching the skin of other people or objects that are contaminated with infectious droplets and then touching your eye(s), nose, or mouth. This can happen when someone who is sick with SARS coughs or sneezes droplets onto themselves, other people, or nearby surfaces.

Scientists at the Centers for Disease Control and Prevention (CDC) and other laboratories have detected a previously unrecognized coronavirus in patients with SARS: SARS-CoV, which is the leading hypothesis for the cause of SARS The sequence of SARS-CoV has been sequenced and all of the sequence, except for the leader sequence, was derived directly from viral RNA. The genome of the SARS coronavirus is 29,727 nucleotides in length and the genome organization is similar to that of other coronaviruses. Open reading frames have been identified that correspond to the predicted polymerase protein (polymerase 1a, 1b), spike protein (S), small membrane protein (E), membrane protein (M) and nucleocapsid protein (N)

Researchers worldwide are been working frantically to develop a treatment for SARS. Currently no treatment has been found to be effective at stopping the SARS-CoV coronavirus associated with SARS. The antiviral drugs currently used, or considered, for treating SARS include ribavirin, 6-azauridine, pyrazofurin, mycophenolic acid, and glycyrrhizin. However, all these drugs have serious side effects (e.g., side effects of glycyrrhizin include raised blood pressure and lowered potassium levels). Treatment with the anti-inflammatory drug methylprednisolone has been shown achieve some improvement in SARS patients (So, L. K., et al., "Development of a standard treatment protocol for severe acute respiratory syndrome", *Lancet* 361(9369): 1615-7, 2003).

Dehydroepiandrosterones are non-glucocorticoid steroids. DHEA, also known as 5androsten-3 beta-ol-17-one and DHEA sulfate (DHEA-S), a sulfated form of DHEA, are endogenous hormones secreted by the adrenal cortex in primates and a few non-primate species in response to the release of ACTH. DHEA is a precursor of both androgen and estrogen steroid hormones important in several endocrine processes. Current medical use of DHEA is limited to controlled clinical trials, and as a food supplement, and is thought to have a role in levels of DHEA in the central nerve system (CNS), and in psychiatric, endocrine, gynecologic, obstetric, immune, and cardiovascular functions.

DHEA-S or its pharmaceutically acceptable salts are believed to improve uterine cervix maturation and uterine musculature sensitivity to oxytocin in late phase pregnancy. DHEA-S and its pharmaceutically acceptable salts are thought to be effective in the therapy for dementia, for the therapy of hyperlipemia, osteoporosis, ulcers, and for disorders associated with high levels of, or high sensitivity to adenosine, such as steroid-dependent asthma, and other respiratory and lung diseases. Dehydroepiandrosterone itself was administered intravenously previously, subcutaneously, percutaneously, vaginally, topically and orally in clinical trials. In preformulation studies, however, the anhydrous form of DHEA sodium sulfate (DHEA-SNa) was found to be unstable to humidity, and its dihydrate form (DHEA-SNa) was found to be more stable under conditions of normal humidity.

As is known, various operations may be performed on medicinal agents during pharmaceutical processing that often affect the physicochemical properties and stability of the compounds. Prolonged grinding of the dehydroepiandrosterone sodium sulfate dihydrate produced a decrease in crystallinity and loss of hydration water; the latter decreasing storage stability and producing DHEA, its degradation product.

Accordingly, there is a need for a powder formulation of dehydroepiandrosterone compounds, their analogues and salts, that will show good dispersibility and shelf stability, as well as appropriate respirable properties. Such formulation would make it possible to deliver the dehydroepiandrosterone compounds, analogues and salts in a highly efficacious and cost effective manner.

U.S. Pat. No. 5,527,789 discloses a method of combating cancer in a subject by administering to the subject dehydroepiandrosterone (DHEA) or DHEA-related compound, and ubiquinone to combat heart failure induced by the DHEA or DHEA-related compound.

U.S. Pat. No. 6,087,351 discloses an in vivo method of reducing or depleting adenosine in a subject's tissue by administering to the subject dehydroepiandrosterone (DHEA) or DHEA-related compound. U.S. Pat. No. 6,087, 351 discloses that solid particulate compositions containing respirable dry particles of micronized active compound may be prepared by grinding dry active compound with a mortar and pestle, and then passing the micronized composition through a 400 mesh screen to break up or separate out large agglomerates. Also, a solid particulate composition comprised of the active compound may optionally contain a dispersant which serves to facilitate the formation of an aerosol; and a suitable dispersant is lactose, which may be blended with the active compound in any suitable ratio (e.g., a 1 to 1 ratio by weight).

DHEA and DHEA-S have been described to treat COPD (U.S. patent application Ser. No. 10/454,061, filed Jun. 3, 2003, and International Application No. PCT/US02/12555, filed Apr. 21, 2002, published Oct. 31, 2002).

SUMMARY OF THE INVENTION

The invention relates to a sealed container containing a powder pharmaceutical composition comprising an agent and a pharmaceutically or veterinarily acceptable carrier or diluent, wherein the agent comprises a dehydroepiandrosterone (DHEA) compound, or analogue thereof, or hydrated form thereof, sealed in a nebulizable form wherein said dry powder pharmaceutical composition is particles of respirable or inhalable size. Preferably, the agent is dehydroepiandrosterone sulfate (DHEA-S), wherein the sulfate is covalently bound to DHEA. More preferably, the agent is dehydroepiandrosterone sulfate dihydrate. Preferably, the dry powder pharmaceutical composition has particles of greater than about 80% of the particles about 0.1 μm to about 100 μm in diameter. The dehydroepiandrosterone compound, or analogue thereof, comprise compounds of chemical formula (I), (II), (III), (IV) and (V), either formulated alone or in combination with a powder, liquid or gaseous carrier. The pharmaceutical composition may or may not further comprise an excipient. The formulation may be administered to a subject together with another therapeutic agent(s), either in the same composition, or by joint administration of separate compositions.

Preferably, the agent is DHEA-S in the dihydrate form (DHEA-S.2H$_2$O). The dihydrate form of DHEA-S is more stable than the anhydrous form of DHEA-S. The anhydrous form of DHEA-S is more heat labile than the dihydrate form of DHEA-S. Preferably, the carrier is lactose. Preferably, the agent is in a powder form. Preferably, the agent is in a crystalline form. More preferably, the agent is in a crystalline powder form.

Preferably, the sealed container is vacuumed sealed and usable for nebulizer to be administered a patient or subject in need of prophylaxis or treatment with a therapeutically effective amount of the powder pharmaceutical composition.

Another aspect of the present invention is a method for prophylaxis or treatment of asthma, comprising administering to a subject in need of such prophylaxis or treatment a therapeutically effective amount of the powder pharmaceutical composition.

Another aspect of the present invention is a method for prophylaxis or treatment of chronic obstructive pulmonary disease, comprising administering to a subject in need of such prophylaxis or treatment a therapeutically effective amount of the powder pharmaceutical composition.

Another aspect of the present invention is a method of reducing or depleting adenosine in a subject's tissue, comprising administering to a subject in need of such treatment a therapeutically effective amount of the powder pharmaceutical composition to reduce or deplete adenosine levels in the subject's tissue.

Another aspect of the present invention is a method for prophylaxis or treatment of a disorder or condition associated with high levels of, or sensitivity to, adenosine in a subject's tissue, comprising administering to a subject in need of such prophylaxis or treatment a therapeutically effective amount of the powder pharmaceutical composition to reduce adenosine levels in the subject's tissue and prevent or treat the disorder.

Preferably, the subject suffers from airway inflammation, allergy, asthma, impeded respiration, cystic fibrosis, Chronic Obstructive Pulmonary Diseases (COPD), allergic rhinitis, Acute Respiratory Distress Syndrome, microbial infection, viral infection, such as SARS, pulmonary hypertension, lung inflammation, bronchitis, airway obstruction, or bronchoconstriction.

Preferably, the dry powder formulation is prepared starting from the dry pharmaceutical agent, altering the particle size of the agent to form a powder formulation of particles greater than about 80% of about 0.1 to about 100 μm in diameter, e.g. altered by milling, e.g. fluid energy milling, sieving, homogenization granulation, and/or other known procedures.

The powder formulation of the invention may be delivered through the respiratory tract by direct administration from a device, either by itself, or along with a powdered, liquid or gaseous carrier or propellant. Preferably, the device is a nebulizer capable of administering the powdered formulation to a patient or subject incapable of inhaling the powdered formulation without the device. The formulation described herein is suitable for treating any diseases; for example those associated with respiratory and lung diseases, such as bronchoconstriction, allergy(ies), asthma, lung inflammation, chronic obstructive pulmonary disease (COPD), allergic rhinitis, ARDS, cystic fibrosis, cancer and inflammation, among others.

Another aspect of the present invention is an use of the dehydroepiandrosterone compound, or analogue thereof, or hydrated form thereof, in the manufacture of a medicament for prophylaxis or treating of asthma, COPD, lung inflammation, any respiratory disorder or condition, or reducing or deleting adenosine in a subject's tissue. Another aspect of the invention is a kit comprising a device for delivering the powder pharmaceutical composition to the subject. Preferably, the device is a nebulizer or aerosolizer, which may be pressurized, either comprising the powder formulation. Preferably, the kit further comprises one or more capsules, cartridges or blisters with the formulation, wherein the capsules, cartridges or blisters are to be inserted in the device prior to use.

BRIEF DESCRIPTION OF THE DRAWINGS

FIG. 1 depicts fine particle fraction of neat micronized DHEA-S.$2H_2O$ delivered from the single-dose Acu-Breathe inhaler as a function of flow rate. Results are expressed as DHEA-S. IDL data on virtually anhydrous micronized DHEA-S are also shown in this figure where the 30 L/min result was set to zero since no detectable mass entered the impactor.

FIG. 2 depicts HPLC chromatograms of virtually anhydrous DHEA-S bulk after storage as neat and lactose blend for 1 week at 50° C. The control was neat DHEA-S stored at room temperature.

FIG. 3 depicts HPLC chromatograms for DHEA-S.$2H_2O$ bulk after storage as neat and lactose blend for 1 week at 50° C. The control was neat DHEA-S.$2H_2O$ stored at room temperature.

FIG. 4 depicts solubility of DHEA-S as a function of NaCl concentration at two temperatures.

FIG. 5 depicts DHEA-S solubility as a function of the reciprocal sodium cation concentration at 24-25° C.

FIG. 6 depicts DHEA-S solubility as a function of the reciprocal sodium cation concentration at 7-8° C.

FIG. 7 depicts solubility of DHEA-S as a function of NaCl concentration with and without buffer at room temperature.

FIG. 8 depicts DHEA-S solubility as a function of the reciprocal of sodium cation concentration at 24-25° C. with and without buffer.

FIG. 9 depicts solution concentration of DHEA-S versus time at two storage conditions.

FIG. 10 depicts solution concentration of DHEA versus time at two storage conditions.

FIG. 11 depicts the schematic for nebulization experiments.

FIG. 12 depicts mass of DHEA-S deposited in by-pass collector as a function of initial solution concentration placed in the nebulizer.

FIG. 13 depicts particle size by cascade impaction for DHEA-S nebulizer solutions.

The data presented are the average of all 7 nebulization experiments.

DETAILED DESCRIPTION OF THE PREFERRED EMBODIMENTS

Glossary

The term "agent", as used herein, means a chemical compound, a mixture of chemical compounds, a synthesized compound, a therapeutic compound, an organic compound, an inorganic compound, a nucleic acid, an oligonucleotide (oligo), a protein, a biological molecule, a macromolecule, lipid, oil, fillers, solution, a cell or a tissue. Agents comprises an active compound(s) that is a DHEA, its derivative or pharmaceutically or veterinarily acceptable salt thereof. Agents may be added to prepare a formulation comprising an active compound and used in a formulation or a kit in a pharmaceutical or veterinary use.

The term "airway", as used herein, means part of or the whole respiratory system of a subject which exposes to air. The airway includes, but not exclusively, throat, windpipes, nasal passages, sinuses, a respiratory tract, lungs, and lung lining, among others. The airway also includes trachea, bronchi, bronchioles, terminal bronchioles, respiratory bronchioles, alveolar ducts, and alveolar sacs.

The term "airway inflammation", as used herein, means a disease or condition related to inflammation on airway of subject. The airway inflammation may be caused or accompanied by allergy(ies), asthma, impeded respiration, cystic fibrosis (CF), Chronic Obstructive Pulmonary Diseases (COPD), allergic rhinitis (AR), Acute Respiratory Distress Syndrome (ARDS), microbial or viral infections, pulmonary hypertension, lung inflammation, bronchitis, airway obstruction, and bronchoconstriction.

The term "carrier", as used herein, means a biologically acceptable carrier in the form of a gaseous, liquid, solid carriers, and mixtures thereof, which are suitable for the different routes of administration intended. Preferably, the carrier is pharmaceutically or veterinarily acceptable.

The composition may optionally comprise other agents such as other therapeutic compounds known in the art for the treatment of the condition or disease, antioxidants, flavoring agents, coloring agents, fillers, volatile oils, buffering agents, dispersants, surfactants, RNA inactivating agents, propellants and preservatives, as well as other agents known to be utilized in therapeutic compositions.

"Composition", as used herein, means a mixture containing a dry powdered formulation comprising an active compound used in this invention and a carrier. The composition may contain other agents. The composition is preferably a pharmaceutical or veterinary composition.

"An effective amount" as used herein, means an amount which provides a therapeutic or prophylactic benefit.

The term "respiratory diseases", as used herein, means diseases or conditions related to the respiratory system. Examples include, but not limited to, airway inflammation, allergy(ies), asthma, impeded respiration, cystic fibrosis (CF), Chronic Obstructive Pulmonary Diseases (COPD), allergic rhinitis (AR), Acute Respiratory Distress Syndrome (ARDS), pulmonary hypertension, lung inflammation, bronchitis, airway obstruction, bronchoconstriction, microbial infection, and viral infection, such as SARS.

"Target", as used herein, means an organ or tissue that the active compound(s) affect and are associated with a disease or condition.

The terms "treat" or "treating", as used herein, mean a treatment which decreases the likelihood that the subject administered such treatment will manifest symptoms of disease or other conditions.

This invention provides a powder formulation comprising a DHEA, its derivatives, and/or its pharmaceutically or veterinarily acceptable salts, or a hydrated form thereof, alone, or along with a pharmaceutically or veterinarily acceptable carrier or diluent, wherein a proportion of the formulation particles about 80% are about 0.1 to about 200 μm in diameter, e.g., greater than about 80% particles. Examples of a DHEA, its analogues and its salts suitable for use in this invention are represented by chemical formulas (I), (II), (III), (IV) and (V) shown below. One group is represented by the compound of chemical formula

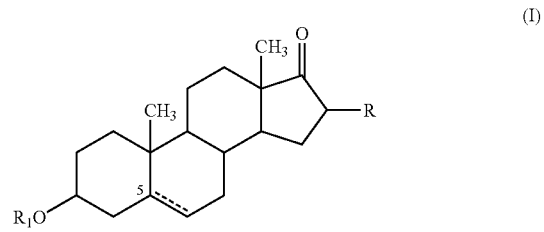

(I)

wherein R comprises H or halogen; the H at position 5 maybe present in the alpha or beta configuration or a racemic mixture of both configurations; and $R_1$ comprises H, or a multivalent inorganic or organic dicarboxylic acid covalently bound to the compound. Preferably, the multivalent inorganic or organic dicarboxylic acid is $SO_2OM$, phosphate or carbonate. Preferably, the multivalent organic dicarboxylic acid is a succinate, maleate, fumarate, or a suitable dicarboyxlate.

M comprises a counterion, for example, H, sodium, potassium, magnesium, aluminum, zinc, calcium, lithium, ammonium, amine, arginine, lysine, histidine, triethylamine, ethanolamine, choline, triethanoamine, procaine, benzathine, tromethanine, pyrrolidine, piperazine, diethylamine, sulphatide

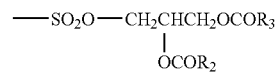

or phosphatide

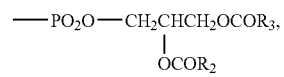

wherein $R_2$ and $R_3$, which may be the same or different, comprise straight or branched ($C_1$-$C_{14}$) alkyl or glucuronide;

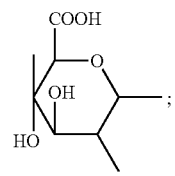

and pharmaceutically acceptable salts thereof.

$R_1$ can be an acidic or basic compound covalently bound to DHEA. If $R_1$ is an acidic compound than the salt is formed by adding a base to the agent. Preferably, the base is any suitable base that would result in the formation of a salt of the agent, such as sodium hydroxide, potassium hydroxide, or the like. If $R_1$ is a basic compound than the salt is formed by adding an acid to the agent. Preferably, the acid is any suitable acid that would result in the formation of a salt of the agent, such as organic acids, such as fumaric acid, maleic acid, lactic acid, or inorganic acids, such as hydrochloric acid, nitric acid, sulfuric acid, or the like.

Preferably, the agent is DHEA-S in the dihydrate form (DHEA-S.2H$_2$O). The dihydrate form of DHEA-S is more stable than the anhydrous form of DHEA-S. The anhydrous form of DHEA-S is more heat labile than the dihydrate form of DHEA-S. Preferably, the carrier is lactose. Preferably, the agent is in a powder form. Preferably, the agent is in a crystalline form. More preferably, the agent is in a crystalline powder form.

The present invention is the first report of using DHEA-S in the dihydrate form in pharmaceutical composition, and that DHEA-S in the dihydrate form has the unexpected property of a better stability, especially at higher temperatures, such as equal or greater than 50° C., than anhydrous DHEA-S. Anhydrous DHEA-S mixed with lactose is much less stable than crystalline dihydrate DHEA-S mixed with lactose. This discovery is reported for the first time in this application (see Examples 3 and 5).

Compounds illustrative of formula (I) above include dehydroepiandrosterone (DHEA), itself wherein R and $R_1$ are each H and the double bond is present; 16-alpha bromoepiandrosterone, where R comprises Br, $R_1$ comprises H, and the double bond is present; 16-alpha-fluoroepiandrosterone, wherein R comprises F, $R_1$ comprises H and double bond is present; etiocholanolone, where R and $R_1$ each comprises hydrogen and the double bond is absent; dehydroepiandrosterone sulfate, wherein R comprises H, $R_1$ comprises SO$_2$OM and M comprises sulphatide as defined above, and the double bond is present; dehydroepiandrosterone sodium sulfate dihydrate, wherein R is H, $R_1$ is SO$_2$OM and M is a sodium group as defined above, and the double bond present, among others. In the compound of formula (I), R preferably comprises halogen e.g., bromo, chloro, or fluoro, $R_1$ comprises H, and the double bond is present, more preferably the compound of formula (I) comprises 16-alpha-fluoro epiandrosterone, the compound of formula (I), wherein R comprises H, $R_1$ comprises SO$_2$OM, M comprises sulphatide and the double bond is present, and more preferably the compound of formula (I) is the dihydrate form of dehydroepiandrosterone sodium sulfate (DHEA-S.2H$_2$O) of chemical formula (II) below.

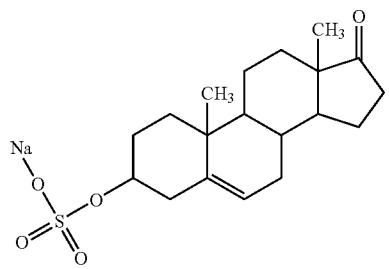

(II)

The compounds of formula (I) and (II) may be synthesized in accordance with known procedures or variations thereof that will be apparent to those skilled in the art. See, for example, U.S. Pat. No. 4,956,355; UK Patent No. 2,240,472; EPO Patent Publication No. 429,187; PCT Patent Publication No. 91/04030; M. Abou-Gharbia et al., J. Pharm. Sci. 70, 1154-1157 (1981); Merck Index Monograph No. 7710; 11th Ed. (1989).

Other examples of a dehydroepiandrosterone derivative, are represented by the compounds of chemical formulas III, IV and V shown below, and their pharmaceutically or veterinarily acceptable salts.

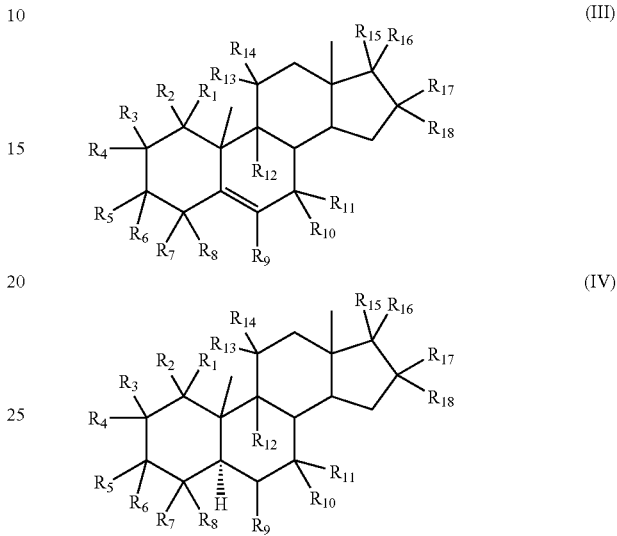

wherein $R_1, R_2, R_3, R_4, R_6, R_7, R_8, R_9, R_{10}, R_{11}, R_{12}, R_{13}$, and $R_{14}$ are independently H, OH, halogen, $C_{1-10}$ alkyl or $C_{1-10}$ alkoxy;

$R_5$ comprises H, OH, halogen, $C_{1-10}$ alkyl, $C_{1-10}$ alkoxy or $OSO_2R_{20}$;

$R_{15}$ comprises (1) H, halogen, $C_{1-10}$ alkyl or $C_{1-10}$ alkoxy when $R_{16}$ comprises $C(O)OR_{21}$, or (2) H, halogen, OH or $C_{1-10}$ alkyl when $R_{16}$ is H, halogen, OH or $C_{1-10}$ alkyl, or (3) H, halogen, $C_{1-10}$ alkyl, $C_{1-10}$ alkenyl, $C_{1-10}$ alkynyl, formyl, $C_{1-10}$ alkanoyl or epoxy when $R_{16}$ comprises OH;

or $R_{15}$ and $R_{16}$ taken together comprise =O; $R_{17}$ and $R_{18}$ comprise independently (1) H, OH, halogen, $C_{1-10}$ alkyl or $C_{1-10}$ alkoxy when $R_{16}$ comprises H, OH, halogen, $C_{1-10}$ alkyl or —C(O)OR$_{21}$, or (2) H, ($C_{1-10}$ alkyl)$_n$ amino, ($C_{1-10}$ alkyl)$_n$ amino-$C_{1-10}$ alkyl, $C_{1-10}$ alkoxy, hydroxy-$C_{1-10}$ alkyl, $C_{1-10}$ alkoxy-$C_{1-10}$ alkyl, (halogen)$_m$-$C_{1-10}$ alkyl, $C_{1-10}$ alkanoyl, formyl, $C_{1-10}$ carbalkoxy or $C_{1-10}$ alkanoyloxy when $R_{15}$ and $R_{16}$ taken together comprise =O; or $R_{17}$ and $R_{18}$ taken together comprise =O or taken together with the carbon to which they are attached form a 3-6 member ring comprising 0 or 1 oxygen atoms; or $R_{15}$ and $R_{17}$ taken together with the carbons to which they are attached form an epoxide ring, $R_{20}$ comprises OH, pharmaceutically acceptable ester or pharmaceutically acceptable ether, $R_{21}$ is H, (halogen)$_m$-$C_{1-10}$ alkyl or $C_{1-10}$ alkyl, n is 0, 1 or 2; and m is 1,2 or 3; with the proviso that (a) $R_3$ is not H, OH or halogen when $R_1, R_2, R_4, R_6, R_7, R_9, R_{10}, R_{12}, R_{13}, R_{14}$, and $R_{17}$ are H and $R_5$ is OH or $C_{1-10}$ alkoxy and $R_8$ is H, OH or halogen and $R_{11}$ is H or OH and $R_{18}$ is H, halogen or methyl and $R_{15}$ is H and $R_{16}$ is OH;

(b) $R_3$ is not H, OH or halogen when $R_1, R_2, R_4, R_6, R_7, R_9, R_{10}, R_{12}, R_{13}$, and $R_{14}$ are H and $R_5$ is OH or $C_{1-10}$ alkoxy and $R_8$ is H, OH or halogen and $R_{11}$ is H or OH and $R_{18}$ is H, halogen or methyl and $R_{15}$ and $R_{16}$ taken together are =O;

(c) $R_5$ is not H, halogen, $C_{1-10}$ alkoxy or $OSO_2R_{20}$ when $R_1$, $R_2$, $R_3$, $R_4$, $R_6$, $R_7$, $R_8$, $R_9$, $R_{10}$, $R_{12}$, $R_{13}$, $R_{14}$ and $R_{17}$ are H and $R_{11}$ is H, halogen, OH or $C_{1-10}$ alkoxy and $R_{18}$ is H or halogen and $R_{15}$ and $R_{16}$ taken together are =O; and (d) $R_5$ is not H, halogen, $C_{1-10}$ alkoxy or $OSO_2R_{20}$ when $R_1$, $R_2$, $R_3$, $R_4$, $R_6$, $R_7$, $R_8$, $R_9$, $R_{10}$, $R_{12}$, $R_{13}$, $R_{14}$ and $R_{17}$ are H and $R_{11}$ is H, halogen, OH or $C_{1-10}$ alkoxy and and $R_{18}$ is H or halogen and $R_{15}$ is H and $R_{16}$ is H, OH or halogen;

or a compound of the chemical formula

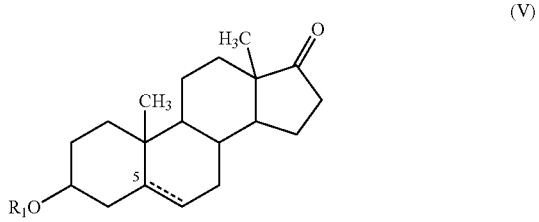

(V)

or pharmaceutically or cosmetically acceptable salts thereof, wherein

R is A—CH(OH)—C(O)— and A comprises H hydrogen or a ($C_1$-$C_{22}$) alkyl or alkenyl which may be substituted with one or more ($C_1$-$C_4$) alkyl, phenyl, halogen or HO groups, the phenyl being optionally with one or more halogen, HO or $CH_3O$.

Compounds of general formulas (III), (IV) and (V) may be synthesized as described in U.S. Pat. Nos. 4,898,694; 5,001,119; 5,028,631; 5,175,154; 6,187,767; and 6,284,750, the relevant portions of which are incorporated herein by reference. The compounds represented by the general formulas (III), (IV) and (V) exist as different stereoisomers and these formulas are intended to encompass each individual stereoisomer and their mixtures.

Examples of representative compounds which fall within the scope of general formulas (III), (IV) and (V) include 5α-androstan-17-one; 16α-fluoro-5α-androstan-17-one; 3β-methyl-5α-androste-17one; 16α-fluoro-5α-androstan-17-one; 17β-bromo-5-androsten-16-one; 17β-fluoro-3β-methyl-5-androsten-16-one; 17α-fluoro-5α-androstan-16-one; 3β-hydroxy-5-androsten-17-one; 17α-methyl-5α-androstan-16-one; 16α-methyl-5-androsten-17-one; 17β, 16α-dimethyl-5-androsten-17-one; 3β,17α-dimethyl-5-androsten-16-one; 16α-hydroxy-5-androsten-17-one; 16α-fluoro-16βmethyl-5-androsten-17-one; 16α-methyl-5α-androstan-17-one; 16-dimethylaminomethyl-5α-androstan-17-one; 16β-methoxy-5-androsten-17-one; 16α-fluoromethyl-5-androsten-17-one; 16-methylene-5-androsten-17-one; 16-cyclopropyl-5α-androstan-17-one; 16-cyclobutyl-5-androsten-17-one; 16-hydroxymethylene-5-androsten-17-one; 3α-bromo-16α-methoxy-5-androsten-17-one; 16-oxymethylene-5-androsten-17-one; 3β-methyl-16xi.-trifluoromethyl-5α-androstan-17-one; 16-carbomethoxy-5-androsten-17-one; 3 β-methyl-16β-methoxy-5α-androstan-17-one; 3β-hydroxy-16α-dimethylamino-5-androsten-17-one; 17α-methyl-5-androsten-17 beta-ol; 17α-ethynyl-5α-androstan-17β-ol; 17β-formyl-5α-androstan-17β-ol; 20,21-epoxy-5α-pregnan-17α-ol; 3β-hydroxy-20,21-epoxy-5α-pregnan-17α-ol; 16α-fluoro-17α-ethenyl-5-androsten-17α-ol; 16α-hydroxy-5-androsten-17α-ol; 16α-methyl-5α-androstan-17α-ol; 16α-methyl-16β-fluoro-5 alpha-androstan-17α-ol; 16α-methyl-16β-fluoro-3-hydroxy-5-androsten-17α-ol; 3β,16 beta-dimethyl-5-androsten-17β-ol; 3β,16,16-trimethyl-5-androsten-17β-ol; 3β,16,16-trimethyl-5-androsten-17-one; 3β-hydroxy-4α-methyl-5-androsten17α-ol; 3β-hy-droxy-4α-methyl-5-androsten-17-one; 3α-hydroxy-1α-methyl-5-androsten-17-one; 3α-ethoxy-5α-androstan-17β-ol; 5α-pregnan-20-one; 3β-methyl-5α-pregnan-20-one; 16α-methyl-5pregnen-20-one; 16α-methyl-3β-hydroxy-5-pregnen-20-one; 17α-fluoro-5-pregnen20-one; 21-fluoro-5α-pregnan-20-one; 17a-methyl-5-pregnen-20-one; 20-acetoxy-cis-17(20)-5α-pregnene; 3α-methyl-16,17-epoxy-5-pregnen-20-one.

The compounds used in this invention may be administered per se or in the form of pharmaceutically and veterinarily acceptable salts; all of these being referred to as "active compounds". Examples of pharmaceutically or veterinarily acceptable carrier or diluent include biologically acceptable carriers, known in the art, including lactose and other inert or G.R.A.S. (generally regarded as safe) agents in gaseous, liquid, or solid form, where the final form of the formulation is as a powder or a powder with a propellant and or co-solvent that may be under pressure.

The powdered formulation may be prepared starting from a dry product comprising a dehydroepiandrosterone, its analogue, its salt or mixtures thereof, by altering the particle size of the agent to form a dry formulation of particle size about 0.01 μm to about 500 μm in diameter; and selecting particles of the formulation comprising at least or greater than about 80%, about 85%, about 90%, about 95%, or about 100% particles of about 0.01 μm, 0.1 μm or 0.5 μm to about 100 μm or 200 μm in diameter. The particle size is desirably less than about 200 μm, preferably in the range about 0.05 μm, about 0.1 μm, about 1 μm, about 2 μm to about 5 μm, about 6 μm, about 8 μm, about 10 μm, about 20 μm, about 50 μm, about 100 μm. Preferably, the selected particles of the formulation of about 0.1 to about 200 μm in diameter. More preferably, the selected particles of the formulation of about 0.1 to about 100 μm in diameter. Even more preferably, the selected particles of the formulation of about 0.1 to about 10 μm in diameter. Even much more preferably, the selected particles of the formulation of about 0.1 to about 8 μm in diameter. Even further much more preferably, the selected particles of the formulation of about 0.1 to about 5 μm in diameter.

The particle size of the dry agent may be then altered so as to permit the absorption of a substantial amount of the agent into the lungs upon inhalation of the formulation. The particle size of the medicament may be reduced by any known means, for example by milling or micronization. Typically, the particle size for the agent is altered by milling the dry agent either alone or in combination with a formulation ingredient to a suitable average particle size, preferably in the about 0.05 μm, about 5 μm range (inhalation) or about 10 μm, to about 50 μm (nasal delivery or lung instillation). Jet milling, also known as fluid energy milling, may be employed and are preferred among the procedures to give the particle size of interest using known devices. Jet milling is the preferred process. It should be understood that although a large percentage of the particles will be in the narrow range desired, this will not generally be true for all particles. Thus, it is expected that the overall particle range may be broader than the preferred range as stated above. The proportion of particles within the preferred range may be greater than about 80%, about 85%, about 90%, about 95%, and so on, depending on the needs of a specific formulation.

The particle size may be also altered by sieving, homogenization, and/or granulation, amongst others. These techniques are used either separately or in combination with one another. Typically, milling, homogenization and granulation are applied, followed by sieving to obtain the dry altered particle size formulation. These procedures may be applied separately to each ingredient, or the ingredients added together and then formulated.

Examples of the formulation ingredients that may be employed are not limited to, but include, an excipient, preservatives, stabilizers, powder flowability improving agents, a cohesiveness improving agent, a surfactant, other bioactive agents, a coloring agent, an aromatic agent, anti-oxidants, fillers, volatile oils, dispersants, flavoring agents, buffering agents, bulking agents, propellants or preservatives. One preferred formulation comprises the active agent and an excipient(s) and/or a propellant(s).

The particle size may be altered not only in a dry atmosphere but also by placing the active agent in solution, suspension or emulsion in inter-mediate steps. The active agent may be placed in solution, suspension, or emulsion, either prior to, or after, altering the particle size of the agent. An example of this embodiment that may be performed by dissolving the agent in a suitable solvent solution, and heating to an appropriate temperature. The temperature may be maintained in the vicinity of the appropriate temperature for a predetermined period of time to allow for crystals to form. The solution and the fledgling crystals then are cooled to a second lower temperature to grow the crystals by maintaining them at the second temperature for a period of time as is known in the art. The crystals are then allowed to reach room temperature when recrystalization is completed and the crystals of the agent have grown sufficiently. The particle size of the agent may also be altered by sample precipitation, which is conducted from solution, suspension or emulsion in an adequate solvent(s).

Spray drying is useful in altering the particle size, as well. By "spray dried or spray drying" what is meant is that the agent or composition is prepared by a process in which a homogeneous mixture of the agent in a solvent or composition termed herein the "pre-spray formulation", is introduced via an atomizer, e.g. a two-fluid nozzle, spinning disk or an equivalent device into a heated atmosphere or a cold fluid as fine droplets. The solution may be an aqueous solution, suspension, emulsion, slurry or the like, as long as it is homogeneous to ensure uniform distribution of the material in the solution and, ultimately, in the powdered formulation. When sprayed into a stream of heated gas or air, the each droplet dries into a solid particle. Spraying of the agent into the cold fluid results in a rapid formation of atomized droplets that form particles upon evaporation of the solvent. The particles are collected, and then any remaining solvent may be removed, generally through sublimation (lyophilization), in a vacuum. As discussed below, the particles may be grown, e.g. by raising the temperature prior to drying. This produces a fine dry powder with particles of a specified size and characteristics, that are more fully discussed below. Suitable spray drying methodologies are also described below. See, for example U.S. Pat. Nos. 3,963,559; 6,451,349; and, 6,458,738, the relevant portions of which are incorporated herein by reference.

As used herein, the term "powder" means a composition that consists of finely dispersed solid particles that are relatively free flowing and capable of being readily dispersed in an inhalation or dry powder device and subsequently inhaled by a patient so that the particles can reach the intended region of the lung. Thus, the powder is "respirable" and suitable for pulmonary delivery. When the particle size of the next agent or the formulation is above about 10 µm, the particles are of such size that a good proportion of them will deposit in the nasal cavities, and will be absorbed there through.

The term "dispersibility" means the degree to which a dry powder formulation may be dispersed, i.e. suspended, in a current of air so that the dispersed particles may be respired or inhaled into the lungs or absorbed through the walls of the nasal cavities of a subject. Thus, a powder that is only 20% dispersible means that only 20% of the mass of particles may be suspended for inhalation into the lungs. The present formulation preferably has a dispersibility of about 1 to 99%, although others are also suitable.

The dry powder formulation may be characterized on the basis of a number of parameters, including, but not limited to, the average particle size, the range of particle size, the fine powder fraction (FPF), the average particle density, and the mass median aerodynamic diameter (MMAD), as is known in the art.

In a preferred embodiment, the agent is DHEA-S in a dihydrate crystalline form. The DHEA-S is first crystallized into the dihydrate crystalline form. The crystals are then put through the jet mill to produce it into a powder form. The preparation can further comprise lactose that is separately sieved or milled and mixed with the powdered crystalline dihydrate DHEA-S.

In a preferred embodiment, the dry powder formulation of this invention is characterized on the basis of their average particle size that was described above. The average particle size of the powdered agent or formulation may be measured as the mass mean diameter (MMD) by conventional techniques. The term, "about" means the numerical values could have an error in the range of about 10% of the numerical value. The dry powdered formulation of this invention may also be characterized on the basis of its fine particle fraction (FPF). The FPF is a measure of the aerosol performance of a powder, where the higher the fraction value, the better. The FPF is defined as a powder with an aerodynamic mass median diameter of less than 6.8 µm as determined using a multiple-stage liquid impinger with a glass throat (MLSI, Astra, Copley Instrument, Nottingham, UK) through a dry powder inhaler (Dryhalter™, Dura Pharmaceuticals). Accordingly, the dry powder formulation of the invention preferably has a FPF of at least about 10%, with at least about 20% being preferred, and at least about 30% being especially preferred. Some systems may enable very high FPFs, of the order of 40 to 50%.

The dry powdered formulation may be characterized also on the basis of the density of the particles containing the agent of the invention. In a preferred embodiment, the particles have a tap density of less than about 0.8 g/cm$^3$, with tap densities of less than about 0.4 g/cm$^3$ being preferred, and a tap density of less than about 0.1 g/cm$^3$ being especially preferred. The tap density of dry powder particles may be measured using a GeoPyc™ (Micrometrics Instruments Corp), as is known in the art. Tap density is a standard measure of the envelope mass density, which is defined generally as the mass of the particle divided by the minimum sphere envelope volume within which it may be enclosed.

In another preferred embodiment, the aerodynamic particle size of the dry powdered formulation may be characterized as is generally outlined in the Examples. Similarly, the mass median aerodynamic diameter (MMAD) of the particles may be evaluated, using techniques well known in the art. The particles may be characterized on the basis of their general morphology as well.

The term "dry" means that the formulation has a moisture content such that the particles are readily dispersible in an inhalation device to form an aerosol. The dry powdered formulation in the invention comprises preferably substantially active compound, although some aggregation may occur, particularly upon long storage periods. As is known for many dry powder formulation, some percentage of the material in a powder formulation may aggregate, this resulting in some loss of activity. Accordingly, the dry powdered formulation has at least about 70% w/w active compound, i.e. % of total compound present, with at least about 80% w/w active compound being preferred, and at least about 90% w/w active compound being especially preferred. More highly active compound or agent is also contemplated, and may be prepared by the present method, i.e., an activity greater than about 95% and higher. The measurement of the total compound present will depend on the compound and, generally, will be done as is known in the art, on the basis of activity assays, etc. The measurement of the activity of the agent will be dependent on the compound and will be done on suitable bioactivity assays as will be appreciated by those in the art.

In spray drying, an individual stress event may arise due to atomization (shear stress and air-liquid interfacial stress), cold or heat denaturation, optionally freezing (ice-water interfacial stress and shear stress), and/or dehydration. Cryoprotectants and lyoprotectants have been used during lyophilization to counter freezing destabilization, and dehydration and long-term storage destabilization, respectively. Cryoprotectant molecules, e.g., sugars, amino acids, polyols, etc., have been widely used to stabilize active compounds in highly concentrated unfrozen liquids associated with ice crystallization. These are not required in the formulation.

The dry powdered formulations comprising an active compound may or not contain an excipient. "Excipients" or "protectants" including cryoprotectants and lyoprotectants generally refers to compounds or materials that are added as diluents or to ensure or increase flowability and aerosol dispersibility of the active compounds during the spray drying step and afterwards, and for long-term flowability of the powdered product. Suitable excipients are generally relatively free flowing particulate solids, do not thicken or polymerize upon contact with water, are basically innocuous when placed in the respiratory tract of a patient and do not substantially interact with the active compound in a manner that alters its biological activity.

Suitable excipients include, but are not limited to, proteins such as human and bovine serum albumin, gelatin, immunoglobulins, carbohydrates including monosaccharides (galactose, D-mannose, sorbose, etc.), disaccharides (lactose, trehalose, sucrose, etc.), cyclodextrins, and polysaccharides (raffinose, maltodextrins, dextrans, etc.); an amino acid such as monosodium glutamate, glycine, alanine, arginine or histidine, as well as hydrophobic amino acids (tryptophan, tyrosine, leucine, phenylalanine, etc.); a lubricant such as magnesium stearate; a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; pluronics; surfactants; (lipid and non-lipid. surfactants) and combinations thereof. Preferred excipients are trehalose, sucrose, sorbitol, and lactose,: as well as mixtures thereof. When excipients are used, they are used generally in amounts ranging from about 0.1, about 1, about 2, about 5, about 10 to about 15, about 10, about 15, about 20, about 40, about 60, about 99% w/w composition. Preferred are formulations containing lactose, or low amounts of excipient or other ingredients.

In another preferred embodiment, the dry powdered formulation of this invention is substantially free of excipients. "Substantially free" in this case generally means that the formulation contains less than about 10%, w/w preferably less than about 5%, w/w more preferably less than about 2-3% w/w, still more preferably less than about 1% w/w of any components other than the agent. Generally, for the purposes of this invention, the formulation may include a propellant and a co-solvent, buffers or salts, and residual water. In one preferred embodiment the dry powdered formulation (prior to the addition of bulking agent, discussed below) consists of the agent and protein as a major component, with small amounts of buffer(s), salt(s) and residual water. Generally, in this embodiment, the spray drying process comprises a temperature raising step prior to drying, as is more fully outlined below.

In another preferred embodiment, the pre-spray dried formulation, i.e. the soiution formulation used in the spray drying process comprises the active agent in solution, e.g. aqueous solution, with only negligible amounts of buffers or other compounds. The pre-spray dried formulation containing little or no excipient may not be highly stable over a long period of time. It is, thus, desirable to perform the spray drying process within a reasonable short time after the pre-spray dried formulation is produced. Although, the pre-spray dried formulation utilizing little or no excipient may not be highly stable, the dry powder made from it may, and generally is both surprisingly stable and highly dispersible, as shown in the Examples.

The agents that are spray dried to form the formulations of the invention comprise the agent and optionally a buffer, and may or may not contain additional salts. The suitable range of the pH of the buffer in solution can be readily ascertained by those in the art. Generally, this will be in the range of physiological pH, although the agent of the invention may flowable at a wider range of pHs, for example acidic pH. Thus, preferred pH ranges of the pre-spray dry formulation are about 1, about 3, about 5, about 6 to about 7, about 8, about 10, and a pH about 7 being especially preferred. As will be appreciated by those in the art, there are a large number of suitable buffers that may be used. Suitable buffers include, but are not limited to, sodium acetate, sodium citrate, sodium succinate, sodium phosphate, ammonium bicarbonate and carbonate. Generally, buffers are used at molarities from about 1 mM, about 2 mM to about 200 mM about 10 mM, about 0.5 M, about 1 M, about 2 M, about 50 M being particularly preferred.

When water, buffers or solvents are used during the preparation process, they may additionally contain salts as already indicated.

In addition, the dry powdered formulation of the invention is generally substantially free of "stabilizers". The formulation may contain, however, an additional surfactant that has its own prophylactic or therapeutic effect on the respiratory system on the lungs. These active agents may compensate for loss of lung surfactant or generally act by other mechanisms. The dry powdered formulations of the invention is also generally substantially free of microsphere-forming polymers. See, e.g. WO 97/44013; U.S. Pat. No. 5,019,400. That is, the powders of the invention generally comprise the active agent(s) and excipient, and do not require the use of polymers for structural or other purposes. The dry powdered formulations of the invention is also preferably stable. "Stability" may mean one of two things, retention of biological activity and retention of dispersibility over time, with preferred embodiments showing stability in both areas.

The dry powdered formulation of the invention generally retains biological activity over time, e.g. physical and chemical stability and integrity upon storage. Losses of biological activity are generally due to aggregation, and/or oxidation of agent's particles. However, when the agent is agglomerate around particles of excipient, the resulting agglomerates are highly stable and active. As will be appreciated by those in the art, there may be an initial loss of biological activity as a result of spray drying, due to the extreme temperatures used in the process. Once this has occurred, however, further loss of activity will be negligible, as measured from the time the powder is made. Moreover, the dry powdered formulation of the invention have been found to retain dispersibility over time, as quantified by the retention of a high FPF over time, the minimally aggregation, caking or clumping observed over time.

The agent(s) of the invention is (are) made by methods known in the art. See, for example, U.S. Pat. Nos. 6,087,351; 5,175,154; and, 6,284,750. The pre-spray drying composition may be formulated for stability as a liquid or solid formulation. For spray drying, the liquid formulations are subjected generally to diafiltration and/or ultrafiltration, as required, for buffer exchange (or removal) and/or concentration, as is known in the art. The pre-spray dry formulations comprise from about 1 mg/ml, about 5 mg/ml, about 10 mg/ml, about 20 mg/ml to about 60 mg/ml, about 75 mg/ml of the agent. Buffers and excipients, if present, are present at concentrations discussed above. The pre-spray drying formulation is then spray dried by dispersing the agent into hot air or gas, or by spraying it into a cold or freezing fluid, e.g. a liquid or gas. The pre-spray dry formulation may be atomized as is known in the art, for example via a two-fluid or ultrasonic nozzle using filtered pressurized air, into, for example, a fluid. Spray drying equipment may be used (Buchi; Niro Yamato; Okawara; Kakoki). It is generally preferable to slightly heat the nozzle, for example by wrapping the nozzle with heating tape to prevent the nozzle head from freezing when a cold fluid is used. The pre-spray dry formulation may be atomized into a cold fluid at a temperature of about −200° C. to about −100° C., about −80° C. The fluid may be a liquid such as liquid nitrogen or other inert fluids, or a gas such as air that is cooled. Dry ice in ethanol may be used as well as supercritical fluids. In one embodiment it is preferred to stir the liquid as the atomization process occurs, although this may not be required.

Micronization techniques involve placing bulk drug into a suitable mill. Such mills are commercially available from, for example, DT Industries, Bristol, Pa., under the tradename STOKES™. Briefly, the bulk drug is placed in an enclosed cavity and subjected to mechanical forces from moving internal parts, e.g., plates, blades, hammers, balls, pebbles, and so forth. Alternatively, or in addition to parts striking the bulk drug, the housing enclosing the cavity may turn or rotate such that the bulk drug is forced against the moving parts. Some mills, e.g., fluid energy or airjet mills, include a high-pressure air stream that forces the bulk powder into the air within the enclosed cavity for contact against internal parts. Once the size and shape of the drug is achieved, the process may be stopped and drug having the appropriate size and shape is recovered. Generally, however, particles having the desired particle size range are recovered on a continuous basis by elutriation.

There are many different types of size reduction techniques that can be used to reduce to size of the particles. There is the cutting method employing the use of a cutter mill that can reduce the size of particles to about 100 µm. There is the compression method employing the use of an end-runner mill that can reduce the size of particles to less than about 50 µm. There is the impact method employing the use of a vibration mill that can reduce the size of particles to about 1 µm or a hammer mill that can reduce the size of particles to about 8 µm. There is the attrition method employing the use of a roller mill that can reduce the size of particles to about 1 µm. There is the combined impact and attrition method employing the use of a pin mill that can reduce the size of particles to about 10 µm, a ball mill that can reduce the size of particles to about 1 µm, a fluid energy mill (or jet mill) that can reduce the size of particles to about 1 µm. One of ordinary skill in the art is able through routine experimentation determine the particle size reduction method and means to produce the desired particle size of the composition.

Supercritical fluid processes may be used for altering the particle size of the agent. Supercritical fluid processes involve precipitation by rapid expansion of supercritical solvents, gas anti-solvent processes, and precipitation from gas-saturated solvents. A supercritical fluid is applied at a temperature and pressure that are greater than its critical temperature ($T_c$) and critical pressure ($P_c$), or compressed fluids in a liquid state. It is known that at near-critical temperatures, large variations in fluid density and transport properties from gas-like to liquid-like can result from relatively moderate pressure changes around the critical pressure (0.9-1.5 $P_c$). While liquids are nearly incompressible and have low diffusivity, gases have higher diffusivity and low solvent power. Supercritical fluids can be made to possess an optimum combination of these properties. The high compressibility of supercritical fluids (implying that large changes in fluid density can be brought about by relatively small changes in pressure, making solvent power highly controllable) coupled with their liquid-like solvent power and better-than-liquid transport properties (higher diffusivity, lower viscosity and lower surface tension compared with liquids), provide a means for controlling mass transfer (mixing) between the solvent containing the solutes (such as a drug) and the supercritical fluid.

The two processes that use supercritical fluids for particle formation and that have received attention in the recent past are: (1) Rapid Expansion of Supercritical Solutions (RESS) (Tom, J. W. Debenedetti, P. G., 1991, The formation of bioerodible polymeric microspheres and microparticles by rapid expansion of supercritical solutions. *BioTechnol. Prog.* 7:403-411), and (2) Gas Anti-Solvent (GAS) Recrystallization (Gallagher, P. M., Coffey, M. P., Krukonis, V. J., and Klasutis, N., 1989, GAS antisolvent recrystallization: new process to recrystallize compounds in soluble and supercritical fluids. *Am. Chem. Sypm.* Ser., No. 406; Yeo et al. (1993); U.S. Pat. No. 5,360,478 to Krukonis et al.; U.S. Pat. No. 5,389,263 to Gallagher et al.). In the RESS process, a solute (from which the particles are formed) is first solubilized in supercritical $CO_2$ to form a solution. The solution is then, for example, sprayed through a nozzle into a lower pressure gaseous medium. Expansion of the solution across this nozzle at supersonic velocities causes rapid depressurization of the solution. This rapid expansion and reduction in $CO_2$ density and solvent power leads to supersaturation of the solution and subsequent recrystallization of virtually contaminant-free particles. The RESS process, however, may not be suited for particle formation from polar compounds because such compounds, which include drugs, exhibit little solubility in supercritical $CO_2$ Cosolvents (e.g., methanol) may be added to $CO_2$ to enhance solubility of polar compounds; this, however, affects product purity and the otherwise environmentally benign nature of the RESS process. The RESS process also suffers from operational and scale-up problems associated with nozzle plugging due to particle accumulation in the nozzle and to freezing of $CO_2$ caused by the Joule-Thompson effect accompanying the large pressure drop.

In the GAS process, a solute of interest (typically a drug) that is in solution or is dissolved in a conventional solvent to form a solution is sprayed, typically through conventional spray nozzles, such as an orifice or capillary tube, into supercritical $CO_2$ which diffuses into the spray droplets causing expansion of the solvent. Because the $CO_2$-expanded solvent has a lower solubilizing capacity than pure solvent, the mixture can become highly supersaturated and the solute is forced to precipitate or crystallize. The GAS process enjoys many advantages over the RESS process. The advantages include higher solute loading (throughput), flexibility of solvent choice, and fewer operational problems in comparison to the RESS process. In comparison to other conventional techniques, the GAS technique is more flexible in the setting of its process parameters, and has the potential to recycle many components, and is therefore more environmentally acceptable. Moreover, the high pressure used in this process (up to 2,500 psig) can also potentially provide a sterilizing medium for processed drug particles; however, for this process to be viable, the selected supercritical fluid should be at least partially miscible with the organic solvent, and the solute should be preferably insoluble in the supercritical fluid.

Gallagher et al. (1989) teach the use of supercritical $CO_2$ to expand a batch volume of a solution of nitroguanadine and recrystallize particles of the dissolved solute. Subsequent studies disclosed by Yeo et al. (1993) used laser-drilled, 25-30 µm capillary nozzles for spraying an organic solution into $CO_2$. Use of 100 µm and 151 µm capillary nozzles also has been reported (Dixon, D. J. and Johnston, K. P., 1993, Formation of microporous polymer fibers and oriented fibrils by precipitation with a compressed fluid antisolvent. *J. App. Polymer Sci*. 50:1929-1942; Dixon, D. G., Luna-Barcenas, G., and Johnson K. P., 1994, Microcellular microspheres and microballoons by precipitation with a vapor-liquid compressed fluid antisolvent. *Polymer* 35:3998-4005).

Examples of solvents are selected from carbon dioxide ($CO_2$), nitrogen ($N_2$), Helium (He), oxygen ($O_2$), ethane, ethylene, ethylene, ethane, methanol, ethanol, trifluoromethane, nitrous oxide, nitrogen dioxide, fluoroform ($CHF_3$), dimethyl ether, propane, butane, isobutanes, propylene, chlorotrifluormethane ($CClF_3$), sulfur hexafluoride ($SF_6$), bromotrifluoromethane ($CBrF_3$), chlorodifluoromethane ($CHClF_2$), hexafluoroethane, carbon tetrafluoride carbon dioxide, 1,1,1,2-tetrafluoroethane, 1,1,1,2,3,3,3-heptafluoropropane, xenon, acetonitrile, dimethylsulfoxide (DMSO), dimethylformamide (DMF), and mixtures of two or more thereof.

The atomization conditions, including atomization gas flow rate, atomization gas pressure, liquid flow rate, etc., are generally controlled to produce liquid droplets having an average diameter of from about 0.5 µm, about 1 µm, about 5 µm to about 10 µm, about 30 µm, about 50 µm, about 100 µm, with droplets of average size about 10 µm and about 5 µm being preferred. Conventional spray drying equipment is generally used. (Buchi, Niro Yamato, Okawara, Kakoki, and the like). Once the droplets are produced, they are dried by removing the water and leaving the active agent, any excipient(s), and residual buffer(s), solvent(s) or salt(s). This may be done in a variety of ways, such as by lyophilization, as is known in the art. i.e. freezing as a cake rather than as droplets. Generally, and preferably, vacuum is applied, e.g. at about the same temperature as freezing occurred. However, it is possible to relieve some of the freezing stress on the agent by raising the temperature of the frozen particles slightly prior to or during the application of vacuum. This process, termed "armealing", reduces agent inactivation, and may be done in one or more steps, e.g. the temperature may be increased one or more times either before or during the drying step of the vacuum with a preferred mode utilizing at least two thermal increases. The particles may be incubated for a period of time, generally sufficient time for thermal equilibrium to be reached, i.e. depending on sample size and efficiency of heat exchange 1 to several hours, prior to the application of the vacuum, then vacuum is applied, and another annealing step is done. The particles may be lyophilized for a period of time sufficient to remove the majority of the water not associated with crystalline structure, the actual period of time depending on the temperature, vacuum strength, sample size, etc.

Spheronization involves the formation of substantially spherical particles and is well known in the art. Commercially available machines for spheronizing drugs are known and include, for example, Marumerizer™ from LCI Corp. (Charlotte, N.C.) and CF-Granulator from Vector Corp. (Marion, Iowa). Such machines include an enclosed cavity with a discharge port, a circular plate and a means to turn the plate, e.g., a motor. Bulk drug or moist granules of drug from a mixer/granulator are fed onto the spinning plate, which forces them against the inside wall of the enclosed cavity. The process results in particles with spherical shape. An alternative approach to spheronization that may be used includes the use of spray drying under controlled conditions. The conditions necessary to spheronize particles using spray-drying techniques are known to those skilled in the art and described in the relevant references and texts, e.g., Remington: The Science and Practice of Pharmacy, Twentieth Edition (Easton, Pa.: Mack Publishing Co., 2000).

In a preferred embodiment, a secondary lyophilization drying step is conducted to remove additional water at temperatures about 0° C., about 10° C., to about 20° C., to about 25° C., with about 20° C. being preferred. The powder is collected then by using conventional techniques, and bulking agents, if desirable, may be added although not required. Once made, the dry powder formulation of the invention may be being readily dispersed by a dry powder inhalation device and subsequently inhaled by a patient so that the particles penetrate into the target regions of the lungs. The powder of the invention may be formulated into unit dosages comprising therapeutically effective amounts of the active agent and used for delivery to a patient, for example, for the prevention and treatment of respiratory and lung disorders.

The dry powder formulation of this invention is formulated and dosed in a fashion consistent with good medical practice, taking into account, for example, the type of disorder being treated, the clinical condition of the individual patient, whether the active agent is administered for preventative or therapeutic purposes, its concentration in the dosage, previous therapy, the patient's clinical history and his/her response to the active agent, the method of administration, the scheduling of administration, the discretion of the attending physician, and other factors known to practitioners. The "effective amount" or "therapeutically effective amount" of the active compound for purposes of this patent include preventative and therapeutic administration, and will depend on the identity of the active agent and is, thus, determined by such considerations and is an amount that increases and maintains the relevant, favorable biological response of the subject being treated. The active agent is suitably administered to a patient at one time or over a series of treatments, preferably once a day, and may be administered to the patient at any time from diagnosis onwards. A "unit dosage" means herein a unit dosage receptacle containing a therapeutically effective amount of a micronized active agent. The dosage receptacle is one that fits within a suitable inhalation device to allow for the aerosolization of the dry powdered formulation by dispersion into a gas stream to form an aerosol. These can be capsules, foil pouches, blisters, vials, etc. The container may be formed from any number of different materials, including plastic, glass, foil, etc, and may be disposable or rechargeable by insertion of a filled capsule, pouch, blister etc. The container generally holds the dry powder formulation, and includes directions for use. The unit dosage containers may be associated with inhalers that will deliver the powder to the patient. These inhalers may optionally have chambers into which the powder is dispersed, suitable for inhalation by a patient.

The dry powdered formulations of the invention may be further formulated in other ways, e.g. as a sustained release composition, for example, for implants, patches, etc. Suitable examples of sustained-release compositions include semipermeable polymer matrices in the form of shaped articles, e.g. films or microcapsules. Sustained-release matrices include for example polylactides. See for example, U.S. Pat. No. 3,773,919; EP 58,481. Copolymers of L-glutamic acid and gamma-ethyl-L-glutamate are also suitable. See, e.g. Sidman et al., Biopolymers 22: 547-556 (1983) as poly(2-hydroxyethyl methacrylate). See Langer et al., J. Biomed. Mater. Res. 15: 167-277 (1981); Langer, Chem. Tech., 12: 98-105 (1982). Also suitable are ethylene vinyl acetate and poly-D-(−)-3-hydroxybutyric acid. See, Langer et al, supra; (EP 133,988). Sustained-release compositions also include liposomally entrapped agent, that may be prepared by known methods. See, for example, DE 3,218,121; Epstein et al., *Proc. Natl. Acad. Sci. USA* 82: 3688-3692 (1985); Hwang et al., *Proc. Natl. Acad. Sci. USA* 77: 4030-4034 (1980); EP 52,322; EP 36,676; EP 88,046; EP 143,949; EP 142,641; Japanese Pat. Application 83-118008; U.S. Pat. Nos. 4,485,045 and 4,544,545; EP 102,324. The relevant sections of all referenced techniques are hereby incorporated by reference. Ordinarily, the liposomes are of the small unilamellar liposomes in about 200 to 800 Angstroms which the lipid content is greater than about 30 mol. % cholesterol, the selected proportion being adjusted for optimal therapy.

In a preferred embodiment, the dry powdered formulation in the invention may not be inhaled but rather injected as a dry powder, using relatively new injection devices and methodologies for injecting powders. In this embodiment, the dispersibility and respirability of the powder is not important, and the particle size may be larger, for example in about 10 μm, about 20 μm to about 40 μm, about 50 μm to about 70 μm, about 100 μm. The dry powdered formulations in the invention may be reconstituted for injection as well. As the powder of the invention shows good stability, it may be reconstituted into liquid form using a diluent and then used in non-pulmonary routes of administration, e.g. by injection, subcutaneously, intravenously, etc. Known diluents may be used, including physiological saline, other buffers, salts, as well as non-aqueous liquids etc. It is also possible to reconstitute the dry powder of the invention and use it to form liquid aerosols for pulmonary delivery, either for nasal or intrapulmonary administration or for inhalation. As used herein, the term “treating” refers to therapeutic and maintenance treatment as well as prophylactic and preventative measures. Those in need of treatment include those already diagnosed with the disorder as well as those prone to having the disorder and those where the disorder is to be prevented. Consecutive treatment or administration refers to treatment on at least a daily basis without interruption in treatment for one or more days. Intermittent treatment or administration, or treatment or administration in an intermittent fashion, refers to treatment that is not consecutive, but rather cyclic in nature. The treatment regime herein may be consecutive or intermittent or of any other suitable mode. The dry powdered formulation may be obtained, for example, by sieving, lyophilization, spray-lyophilization, spray drying, and freeze drying, etc. These methods may be combined for improved effect. Filters may be employed for sieving, as will be known to a skilled artisan. The alteration and selection of the agent’s particle size may be conducted in a single step, preferably, by micronizing under conditions effective to attain the desired particle size as previously described.

The dry powdered formulation may be then stored under controlled conditions of temperature, humidity, light, pressure etc., so long as the flowability of the agent is preserved. The agent’s stability upon the storing may be measured at a selected temperature for a selected time period and for rapid screening a matrix of conditions are run, e.g. at 2-8° C., 30° C. and sometimes 40° C., for periods of 2, 4 and 24 weeks. The length of time and conditions under which a formulation should be stable will depend on a number of factors, including the above, amount made per batch, storage conditions, turnover of the product, etc. These tests are usually done at 38% (rh) relative humidity. Under these conditions, the agent generally loses less than about 30% biological activity over 18 months, sometimes less than about 20%, or less than about 10%. The dry powder of the invention loses less than about 50% FPF, in some cases less than about 30%, and in others less than about 20%.

The dry powder formulation of the invention may be combined with formulation ingredients, such as bulking agents or carriers, which are used to reduce the concentration of the agent in the dry powder being delivered to a patient. The addition of these ingredients to the formulation is not required, however, in some cases it may be desirable to have larger volumes of material per unit dose. Bulking agents may also be used to improve the flowability and dispersibility of the powder within a dispersion device, or to improve the handling characteristics of the powder. This is distinguishable from the use of bulking agents or carriers during certain particle size reduction processes (e.g. spraying drying). Suitable bulking agents or excipients are generally crystalline (to avoid water absorption) and include, but are not limited to, lactose and mannitol. If lactose, is added, for example, in amounts of about 99: about 1: about 5: active agent to bulking agent to about 1:99 being preferred, and from about 5 to about 5: and from about 1:10 to about 1:20.

The dry powder formulations of the invention may contain other drugs, e.g., combinations of therapeutic agents may be processed together, e.g. spray dried, or they may be processed separately and then combined, or one component may be spray dried and the other may not, while it is processed in one of the other manners enabled herein. The combination of drugs will depend on the disorder for which the drugs are given, as will be appreciated by those in the art. The dry powder formulation of the invention may also comprise, as formulation ingredients, excipients, preservatives, detergents, surfactants, antioxidants, etc, and may be administered by any means that transports the agent to the airways by any suitable means, but are preferably administered through the respiratory system as a respirable formulation, more preferably in the form of an aerosol or spray comprising the agent’s particles, and optionally, other therapeutic agents and formulation ingredients.

In another embodiment, the dry powdered formulations may comprise the dry pharmaceutical agent of this invention and one or more surfactants. Suitable surfactants or surfactant components for enhancing the uptake of the active compounds used in the invention include synthetic and natural as well as full and truncated forms of surfactant protein A, surfactant protein B, surfactant protein C, surfactant protein D and surfactant protein E, disaturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine, phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamelar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric- and polymeric-, poly(vinylamine) with dextran and/or alkanoyl side chains, Brij 35®, Triton X-100®, and synthetic surfactants ALEC®, Exosurt®, Survan®, and Atovaquone®, among others. These surfactants may be used either as single or part of a multiple component surfactant in a formulation, or as covalently bound additions to the active compounds.

Examples of other therapeutic agents for use in the present formulation are analgesics such as Acetaminophen, Anilerdine, Aspirin, Buprenorphine, Butabital, Butorpphanol, Choline Salicylate, Codeine, Dezocine, Diclofenac, Diflunisal, Dihydrocodeine, Elcatoninin, Etodolac, Fenoprofen, Hydrocodone, Hydromorphone, Ibuprofen, Ketoprofen, Ketorolac, Levorphanol, Magnesium Salicylate, Meclofenamate, Mefenamic Acid, Meperidine, Methadone, Methotrimeprazine, Morphine, Nalbuphine, Naproxen, Opium, Oxycodone, Oxymorphone, Pentazocine, Phenobarbital, Propoxyphene, Salsalate, Sodium Salicylate, Tramadol and Narcotic analgesics in addition to those listed above. See, Mosby's Physician's GenRx.

Anti-anxiety agents are also useful including Alprazolam, Bromazepam, Buspirone, Chlordiazepoxide, Chlormezanone, Clorazepate, Diazepam, Halazepam, Hydroxyzine, Ketaszolam, Lorazepam, Meprobamate, Oxazepam and Prazepam, among others. Anti-anxiety agents associated with mental depression, such as Chlordiazepoxide, Amitriptyline, Loxapine Maprotiline and Perphenazine, among others. Anti-inflammatory agents such as non-rheumatic Aspirin, Choline Salicylate, Diclofenac, Diflunisal, Etodolac, Fenoprofen, Floctafenine, Flurbiprofen, Ibuprofen, Indomethacin, Ketoprofen, Magnesium Salicylate, Meclofenamate, Mefenamic Acid, Nabumetone, Naproxen, Oxaprozin, Phenylbutazone, Piroxicam, Salsalate, Sodium Salicylate, Sulindac, Tenoxicam, Tiaprofenic Acid, Tolmetin, anti-inflammatories for ocular treatment such as Diclofenac, Flurbiprofen, Indomethacin, Ketorolac, Rimexolone (generally for postoperative treatment), anti-inflammatories for, non-infectious nasal applications such as Beclomethaxone, Budesonide, Dexamethasone, Flunisolide, Triamcinolone, and the like. Soporifics (anti-insomnia/sleep inducing agents) such as those utilized for treatment of insomnia, including Alprazolam, Bromazepam, Diazepam, Diphenhydramine, Doxylamine, treatments such as Tricyclic Antidepressants, including Amitriptyline HCl (Elavil), Amitriptyline HCl, Perphenazine (Triavil) and Doxepin HCl (Sinequan). Examples of tranquilizers Estazolam, Flurazepam, Halazepam, Ketazolam, Lorazepam, Nitrazepam, Prazepam Quazepam, Temazepam, Triazolam, Zolpidem and Sopiclone, among others. Sedatives including Diphenhydramine, Hydroxyzine, Methotrimeprazine, Promethazine, Propofol, Melatonin, Trimeprazine, and the like.

Sedatives and agents used for treatment of petit mal and tremors, among other conditions, such as Amitriptyline HCl; Chlordiazepoxide, Amobarbital; Secobarbital, Aprobarbital, Butabarbital, Ethchiorvynol, Glutethimide, L-Tryptophan, Mephobarbital, MethoHexital Na, Midazolam HCl, Oxazepam, Pentobarbital Na, Phenobarbital, Secobarbital Na, Thiamylal Na, and many others. Agents used in the treatment of head trauma (Brain Injury/Ischemia), such as Enadoline HCl (e.g. for treatment of severe head injury; orphan status, Warner Lambert), cytoprotective agents, and agents for the treatment of menopause, menopausal symptoms (treatment), e.g. Ergotamine, Belladonna Alkaloids and Phenobarbital, for the treatment of menopausal vasomotor symptoms, e.g. Clonidine, Conjugated Estrogens and Medroxyprogesterone, Estradiol, Estradiol Cypionate, Estradiol Valerate, Estrogens, conjugated Estrogens, esterified Estrone, Estropipate, and Ethinyl Estradiol. Examples of agents for treatment of pre-menstrual syndrome (PMS) are Progesterone, Progestin, Gonadotrophic Releasing Hormone, Oral contraceptives, Danazol, Luprolide Acetate, Vitamin B6. Examples of agents for treatment of emotional/psychiatric, anti-depressants and anti-anxiety agents are Diazepam (Valium), Lorazepam (Ativan), Alprazolam (Xanax), SSRI's (selective Serotonin reuptake inhibitors), Fluoxetine HCl (Prozac), Sertaline HCl (Zoloft), Paroxetine HCl (Paxil), Fluvoxamine Maleate (Luvox), Venlafaxine HCl (Effexor), Serotonin, Serotonin Agonists (Fenfluramine), and other over the counter (OTC) medications.

Such combination therapeutic formulations can be manufactured using many conventional techniques. It may be necessary to micronize the active compounds and if appropriate (i.e. where an ordered mixture is not intended) any carrier in a suitable mill, for example in a jet mill at some point in the process, in order to produce primary particles in a size range appropriate for maximal deposition in the lower respiratory tract (i.e., from about 0.1 µm to about 10 µm). For example, one can dry mix DHEA and carrier, where appropriate, and then micronize the substances together; alternatively, the substances can be micronized separately, and then mixed. Where the compounds to be mixed have different physical properties such as hardness and brittleness, resistance to micronization varies and they may require different pressures to be broken down to suitable particle sizes. When micronized together, therefore, the obtained particle size of one of the components may be unsatisfactory. In such case it would be advantageous to first micronize the different components separately and then mix them.

It is also possible first to dissolve the active component including, where an ordered mixture is not intended, any carrier in a suitable solvent, e.g. water, to obtain mixing on the molecular level. This procedure also makes it possible to adjust the pH-value to a desired level. The pharmaceutically accepted limits of pH 3.0 to 8.5 for inhalation products must be taken into account, since products with a pH outside these limits may induce irritation and constriction of the airways. To obtain a powder, the solvent must be removed by a process which retains the biological activity of DHEA. Suitable drying methods include vacuum concentration, open drying, spray drying, freeze drying and use of supercritical fluids. Temperatures over 50° C. for more than a few minutes should generally be avoided, as some degradation of the DHEA may occur. After drying step the solid material can, if necessary, be ground to obtain a coarse powder, and then, if necessary, micronized.

If desired, the micronized powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range.

Where an ordered mixture is desired, the active compound may be processed, for example by micronization, in order to obtain, if desired, particles within a particular size range. The carrier may also be processed, for example to obtain a desired size and desirable surface properties, such as a particular surface to weight ratio, or a certain texture, and to ensure optimal adhesion forces in the ordered mixture. Such physical requirements of an ordered mixture are well known, as are the various means of obtaining an ordered mixture which fulfils the said requirements, and may be determined easily by one skilled in the art.

The dry powder formulation of this invention may be administered into the respiratory tract as a formulation of respirable size particles i.e. particles of a size sufficiently small to pass through the nose, mouth, larynx or lungs upon inhalation, nasal administration or lung instillation, to the bronchi and alveoli of the lungs. In general, respirable particles range from about 0.1 μm to about 100 μm, and inhalable particles are about 0.1 μm to about 10 μm, to about 5 μm in size. Mostly, when inhaled, particles of non-respirable size that are included in the aerosol tend to deposit in the throat and be swallowed, which reduces the quantity of nonrespirable particles in the aerosol. For nasal administration, a particle size in the range of about 10 μm to about 20 μm, about 50 μm, about 60 μm, or about 100 μm, is preferred to ensure retention in the nasal cavity.

The size and shape of the particles may be analyzed using known techniques for determine and ensure proper particle morphology. For example, one skilled in the art can visually inspect the particles under a microscope and/or determine particle size by passing them through a mesh screen. Preferred techniques for visualization of particles include scanning electron microscopy (SEM) and transmission electron microscopy (TEM). Particle size analysis may take place using laser diffraction methods. Commercially available systems for carrying out particle size analysis by laser diffraction are available from Clausthal-Zellerfeld, Germany (HELOS H1006).

The dry powdered formulation of the invention may be delivered with any device that generates solid particulate aerosols, such as aerosol or spray generators. These devices produce respirable particles, as explained above, and generate a volume of aerosol or spray containing a predetermined metered dose of a medicament at a rate suitable for human or animal administration. One illustrative type of solid particulate aerosol or spray generator is an insufflator, which are suitable for administration of finely comminuted powders. The latter may be taken also into the nasal cavity in the manner of a snuff. In the insufflator, the powder, e.g. a metered dose of the agent effective to carry out the treatments described herein, is contained in a capsule or a cartridge. These capsules or cartridges are typically made of gelatin, foil or plastic, and may be pierced or opened in situ, and the powder delivered by air drawn through the device upon inhalation or by means of a manually-operated pump. The dry powder formulation employed in the insufflator may consist either solely of the agent or of a powder blend comprising the agent, and the agent typically comprises from 0.01 to 100% w/w of the formulation. The dry powdered formulation generally contains the active compound in an amount of about 0.01% w/w, about 1% w/w/, about 5% w/w, to about 20%, w/w, about 40% w/w, about 99.99% w/w. Other ingredients, and other amounts of the agent, however, are also suitable within the confines of this invention.

In a preferred embodiment, the dry powdered formulation is delivered by a nebulizer. This is means is especially useful for patients or subjects who are unable to inhale or respire the powder pharmaceutical composition under their own efforts. In serious cases, the patients or subjects are kept alive through artificial respirator. The nebulizer can use any pharmaceutically or veterinarily acceptable carrier, such as a weak saline solution. Preferably, the weak saline solution is less than about 1.0 or 0.5% NaCl. More preferably, the weak saline solution is less than about 0.2% or 0.15% NaCl. Even more preferably, the weak saline solution is less than about 0.12% NaCl. The nebulizer is the means by which the powder pharmaceutical composition is delivered to the target of the patients or subjects in the airways. The stability of anhydrous compounds, such as anhydrous DHEA-S, can be maintained or increased by eliminating or reducing the water content within the sealed container, e.g. vial, containing the compound. Preferably, besides the compound, it is a vacuum within the sealed container.

The formulation of the invention is also provided in various forms that are tailored for different methods of administration and routes of delivery. The formulations that are contemplated are, for example, a transdermal formulation also containing an excipient and other agents suitable for delivery through the skin, mouth, nose, vagina, anus, eyes, and other body cavities, intradermally, as a sustained release formulation, intrathecally, intravascularly, by inhalation, nasally, intrapulmonarily, into an organ, by implantation, by suppositories, as cremes, gels, and the like, all known in the art. In one embodiment, the dry powdered formulation comprises a respirable formulation, such as an aerosol or spray. The dry powder formulation of the invention is provided in bulk, and in unit form, as well as in the form of an implant, a capsule, blister or cartridge, which may be openable or piercable as is known in the art. A kit is also provided, that comprises a delivery device, and in separate containers, the dry powdered formulation of the invention, and optionally other excipient and therapeutic agents, and instructions for the use of the kit components.

In one preferred embodiment, the agent is delivered using suspension metered dose inhalation (MDI) formulation. Such a MDI formulation can be delivered using a delivery device using a propellant such as hydrofluroalkane (HFA). Preferably, the HFA propellants contain 100 parts per million (PPM) or less of water. N. C. Miller (In: Respiratory Drug Delivery, P. R. Bryon (ed.), CRC Press, Boca Raton, 1990, pp. 249-257) reviewed the effect of water content on crystal growth in MDI suspensions. When exposed to water, anhydrous DHEA-S will hydrate and eventually form large particles. This hydration process can happen in a suspension of the anhydrous DHEA-S in an HFA propellant which has a water content. This hydration process would accelerate the crystal growth due to the formation of strong interparticle bonds and cause the formation of large particles. In contrast, the dihydrate form is already hydrated thus more stable, and thus more preferred, than the anyhydrous form in a MDI, as the dihydrate form will not further form larger particles. If DHEA-S forms a solvate with a HFA propellant that has a lower energy than the dihydrate form, then this DHEA-S solvate would be the most stable, and hence more preferred, form for an MDI.

In one preferred embodiment, the delivery device comprises a dry powder inhalator (DPI) that delivers single or multiple doses of the formulation. The single dose inhalator may be provided as a disposable kit which is sterilely preloaded with enough formulation for one application. The inhalator may be provided as a pressurized inhalator, and the formulation in a piercable or openable capsule or cartridge. The kit may optionally also comprise in a separate container an agent such as other therapeutic compounds, excipients, surfactants (intended as therapeutic agents as well as formulation ingredients), antioxidants, flavoring and coloring agents, fillers, volatile oils, buffering agents, dispersants, surfactants, antioxidants, flavoring agents, bulking agents, propellants and preservatives, among other suitable additives for the different formulations. The dry powdered formulation of this invention may be utilized by itself or in the form of a composition or various formulations in the treatment and/or prevention of a disease or condition associated with bronchoconstriction, allergy(ies), lung cancer and/or inflammation. Examples of diseases are airway inflammation, allergy (ies), asthma, impeded respiration, CF, COPD, AR,ARDS, pulmonary hypertension, lung inflammation, bronchitis, airway obstruction, bronchoconstriction, microbial infection, viral infection (such as SARS), among others. Clearly the present formulation may be administered for treating any disease that afflicts a subject, with the above just being examples. Typically, the dry powdered formulation may be administered in an amount effective for the agent to reduce or improve the symptom of the disease or condition.

The dry powdered formulation may be administered directly to the lung(s), preferably as a respirable powder, aerosol or spray. Although an artisan will know how to titrate the amount of dry powdered formulation to be administered by the weight of the subject being treated in accordance with the teachings of this patent, the agent is preferably administered in an amount effective to attain an intracellular concentration of about 0.05 to about 10 µM agent, and more preferably up to about 5 µM. Propellants may be employed under pressure, and they may also carry co-solvents. The dry powdered formulation of the invention may be delivered in one of many ways, including a transdermal or systemic route, orally, intracavitarily, intranasally, intraanally, intravaginally, transdermally, intrabucally, intravenously, subcutaneously, intramuscularly, intratumorously, into a gland, by implantation, intradermally, and many others, including as an implant, slow release, transdermal release, sustained release formulation and coated with one or more macromolecules to avoid destruction of the agent prior to reaching the target tissue. Subject that may be treated by this agent include humans and other animals in general, and in particular vertebrates, and amongst these mammals, and more specifically and small and large, wild and domesticated, marine and farm animals, and preferably humans and domesticated and farm animals and pets.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The relevant portions of all references cited herein are incorporated by reference in their entirety. In these examples, µM means micromolar, mM means millimolar, ml means milliliters, pm or micron means micrometers, mm means millimeters, cm means centimeters, ° C. means degrees Celsius, µg means micrograms, mg means milligrams, g means grams, kg means kilograms, M means molar, and h means hours.

EXAMPLES

Example 1

Airjet Milling of Anhydrous DHEA-S & Determination of Respirable Dose

DHEA-S is evaluated as a once-per-day asthma therapy alternative to inhaled corticosteroid treatment that is not expected to share the safety concerns associated with that class. The solid-state stability of DHEA-S, sodium dehydroepiandrostenone sulfate (NaDHEA-S) or sodium prasterone sulfate, has been studied for both bulk and milled material (Nakagawa, H., Yoshiteru, T., and Fujimoto, Y. (1981) Chem. Pharm. Bull. 29(5) 1466-1469; Nakagawa, H., Yoshiteru, T., and Sugimoto, I. (1982) Chem. Pharm. Bull. 30(1) 242-248). DHEA-S is most stable and crystalline as the dihydrate form. The DHEA-S anhydrous form has low crystallinity and is very hygroscopic. The DHEA-S anhydrous form is stable as long as it picks up no water on storage. Keeping a partially crystalline material free of moisture requires specialized manufacturing and packing technology. For a robust product, minimizing sensitivity to moisture is essential during the development process.

(1) Micronization of DHEA-S

Anhydrous DHEA sulfate was micronized using a jet milling (Jet-O-Mizer Series #00, 100-120 PSI nitrogen). Approximately 1 g sample was passed through the jet mill, once, and approximately 2 g sample were passed through the jet mill twice. The particles from each milling run were suspended in hexane, in which DHEA-S was insoluble and Spa85 surfactant added to prevent agglomeration. The resulting solution was sonicated for 3 minutes and appeared fuilly dispersed. The dispersed solutions were tested on a Malvern Mastersizer X with a small volume sampler (SVS) attachment. One sample of dispersed material was tested 5 times. The median particle size or D(v, 0.5) of unmilled material was 52.56 µm and the % RSD (relative standard deviation) was 7.61 for the 5 values. The D(v, 0.5) for a single pass through the jet mill was 3.90 µm and the % RSD was 1.27, and the D(v, 0.5) from a double pass through the jet mill 3.25 µm and the % RSD was 3.10. This demonstrates that DHEA-S can be jet milled to particles of size suitable for inhalation.

(2) HPLC Analysis

Two vials (A; single-pass; 150 mg) and (B double-pass; 600 mg) of the micronized drug were available for determining drug degradation during jet milling micronization. Weighed aliquots of DHEA-S from vials A and B were compared to a standard solution of unmilled DHEA-S (10 mg/ml) in an acetonitrile-water solution (1:1). The chromatographic peak area for the HPLC assay of the unmilled drug standard solution (10 mg/ml) gave a value of 23,427. Weighed aliquots of micronized DHEA-S form vials A and B, (5 mg/ml) was prepared in an acetonitrile-water solution (1:1). The chromatographic peak areas for vials A and B were 11,979 and 11,677, respectively. Clearly, there was no detectable degradation of the drug during the jet milling micronization process.

(3) Emitted Dose Studies

DHEA-S powder was collected in Nephele tubes and assayed by HPLC. Triplicate experiments were performed at each airflow rate for each of the three dry powder inhalers tested (Rotahaler, Diskhaler and IDL's DPI devices). A Nephele tube was fitted at one end with a glass filter (Gelman Sciences, Type A/E, 25 µm), which in turn was connected to the airflow line to collect the emitted dose of the drug from the respective dry powder inhaler being tested. A silicone adapter, with an opening to receive the mouthpiece of the respective dry powder inhaler being tested at the other end of the Nephele tube was secured. A desired airflow, of 30, 60, or 90 L/min, was achieved through the Nephele tube. Each dry powder inhaler's mouthpiece was inserted then into the silicone rubber adapter, and the airflow was continued for about four sees after which the tube was removed and an end-cap screwed onto the end of each tube. The endcap of the tube not containing the filter was removed and 10 ml of an HPLC grade water-acetonitrile solution (1:1) added to the tube, the end-cap reattached, and the tube shaken for 1-2 minutes. The end-cap then was removed from the tube and the solution was transferred to a 10 ml plastic syringe fitted with a filter (Cameo 13N Syringe Filter, Nylon, 0.22 μm). An aliquot of the solution was directly filtered into an HPLC vial for later drug assay via HPLC. The emitted dose experiments were performed with micronized DHEA-S (about 12.5 or 25 mg) being placed in either a gelatin capsule (Rotahaler) or a Ventodisk blister (Diskhaler and single-dose DPI (IDL)). When the micronized DHEA-S (only vial B used), was weighed for placement into the gelatin capsule or blister, there appeared to be a few aggregates of the micronized powder. The results of the emitted dose tests conducted at an airflow rate of 30, 60 and 87.8 L/min are displayed in Tables 1 through 4. Table 1 contains the results for Rotahaler experiments at 3 different flow rates. Table 2 contains the results for Diskhaler experiments at 3 different flow rates, and Table 3 contains the results of multi-dose experiments at 3 different flow rates. Table 4 summarizes the results of the experiments.

TABLE 1

Emitted Dose with Rotahaler

| Inhaler Device | Airflow Rate (L/min) | Drug Fill Weight (mg) | Emitted Dose (%) |
|---|---|---|---|
| Rotahaler | 87.8 | 25.4 | 73.2 |
|  | 87.8 | 25.0 | 67.1 |
|  | 87.8 | 24.8 | 68.7 |
| Average |  |  | 69.7 |
| Rotahaler | 87.8 | 13.3 | 16.0 |
|  | 87.8 | 14.1 | 24.5 |
|  | 87.8 | 13.3 | 53.9 |
| Average |  |  | 31.5 |
| Rotahaler | 60 | 13.2 | 58.1 |
|  | 60 | 13.3 | 68.2 |
|  | 60 | 13.7 | 45.7 |
| Average |  |  | 57.3 |
| Rotahaler | 30 | 13.0 | 34.5 |
|  | 30 | 13.0 | 21.2 |
|  | 30 | 13.2 | 48.5 |
| Average |  |  | 34.7 |

TABLE 2

Emitted Dose with Diskhaler

| Inhaler Device | Airflow Rate (L/min) | Drug Fill Weight (mg) | Emitted Dose (%) |
|---|---|---|---|
| Diskhaler | 87.8 | 25.5 | 65.7 |
|  | 87.8 | 25.0 | 41.6 |
|  | 87.8 | 25.2 | 46.5 |
| Average |  |  | 51.3 |
| Diskhaler | 87.8 | 14.1 | 57.9 |
|  | 87.8 | 13.5 | 59.9 |
|  | 87.8 | 13.9 | 59.5 |
| Average |  |  | 59.1 |
| Diskhaler | 60 | 13.1 | 63.4 |
|  | 60 | 13.3 | 38.9 |
|  | 60 | 13.3 | 58.0 |
| Average |  |  | 53.4 |
| Diskhaler | 60 | 13.4 | 68.2 |
| Diskhaler | 30 | 13.4 | 53.8 |
|  | 30 | 13.6 | 53.4 |
|  | 30 | 13.2 | 68.7 |
| Average |  |  | 58.6 |

TABLE 3

IDL Multi-Dose Emitted Dose Experiments

| Inhaler Device | Airflow Rate (L/min) | Drug Fill Weight (mg) | Emitted Dose (%) |
|---|---|---|---|
| IDL Multi-dose | 87.8 | 13.6 | 71.3 |
|  | 87.8 | 13.5 | 79.0 |
|  | 87.8 | 13.4 | 67.4 |
| Average |  |  | 72.6 |
| IDL Multi-dose | 87.8 | 12.9 | 85.7 |
|  | 87.8 | 13.4 | 84.6 |
|  | 87.8 | 13.0 | 84.0 |
| Average |  |  | 84.8 |
| IDL Multi-dose | 60 | 12.6 | 78.8 |
|  | 60 | 12.7 | 83.7 |
|  | 60 | 12.9 | 89.6 |
| Average |  |  | 84.0 |
| IDL Multi-dose | 30 | 13.1 | 78.9 |
|  | 30 | 13.1 | 88.2 |
|  | 30 | 13.1 | 89.2 |
| Average |  |  | 85.4 |

TABLE 4

Emitted Dose Comparison of Three Different Dry Powder Inhaler Devices

| Inhaler Device | Airflow Rate (L/min) | Emitted Dose (%) |
|---|---|---|
| Rotahaler | 87.8 | 73.2, 67.1, 68.7 |
| Average |  | 69.7 |
| Rotahaler (2nd study) | 87.8 | 16.0, 24.5, 53.9 |
| Average |  | 31.5 |
| Diskhaler | 87.8 | 65.7, 41.6, 46.5 |
| Average |  | 51.3 |
| Diskhaler (2nd study) | 87.8 | 57.9, 59.9, 59.5 |
| Average |  | 59.1 |
| IDL Multi-Dose | 87.8 | 71.3, 79.0, 67.4 |
| Average |  | 72.6 |
| IDL Multi-Dose (2nd study) | 87.8 | 85.7, 84.6, 84.0 |
| Average |  | 84.8 |
| Rotahaler | 60 | 58.1, 68.2, 45.7 |
| Average |  | 57.3 |
| Diskhaler | 60 | 63.4, 38.9, 58.0 |
| Average |  | 68.2 |
| IDL Multi-Dose | 60 | 78.8, 83.7, 89.6 |
| Average |  | 84.0 |
| Rotahaler | 30 | 34.5, 21.2, 48.5 |
| Average |  | 34.7 |
| Diskhaler | 30 | 53.8, 53.4, 68.7 |
| Average |  | 58.6 |
| IDL Multi-Dose | 30 | 78.9, 88.2, 89.2 |
| Average |  | 85.4 |

(4) Respirable Dose Studies

The respirable dose (respirable fraction) studies were performed using a standard sampler cascade impactor (Andersen), consisting of an inlet cone (an impactor pre-separator was substituted here), 9 stages, 8 collection plates, and a backup filter within 8 aluminum stages held together by 3 spring clamps and gasket O-ring seals, where each impactor stage contains multiple precision drilled orifices. When air is drawn through the sampler, multiple jets of air in each stage direct any airborne particles toward the surface of the collection plate for that stage. The size ,of the jets is constant for each stage, but is smaller in each succeeding stage. Whether a particle is impacted on any given stage depends upon its aerodynamic diameter. The range of particle sizes collected on each stage depends upon on the jet velocity of the stage, and the cutoff point of the previous stage. Any particle not collected on the first stage follows the air stream around the edge of the plate to the next stage, where it is either impacted or passed on to the succeeding stage, and so on, until the velocity of the jet is sufficient for impaction. To prevent particle bounce during the cascade impactor test, the individual impactor plates were coated with a hexane-grease (high vacuum) solution (100:1 ratio). As noted above, the particle size cut-off points on the impactor plates changed at different airflow rates. For example, Stage 2 corresponds to a cut-off value greater than 6.2 μm particles at 60 L/min, and greater than 5.8 μm particles at 30 L/min, and stage 3 had a particle size cut-off value at 90 L/min greater than 5.6 μm. Thus, similar cut-off particle values are preferentially employed at comparable airflow rates, i.e. ranging from 5.6 to 6.2 μm. The set-up recommended by the United States Phamacopeia for testing dry powder inhalers consists of a mouthpiece adapter (silicone in this case) attached to a glass throat (modified 50 ml round-bottom flask) and a glass distal pharynx (induction port) leading top the pre-separator and Andersen sampler. The pre-separator sample includes washings from the mouthpiece adaptor, glass throat, distal glass pharynx and pre-separator. 5 ml acetonitrile:water (1:1 ratio) solvent was placed in the pre-separator before performing the cascade impactor experiment, that were performed in duplicate with 3 different dry powder inhaler devices and at 3 airflow rates, 30, 60 and 90 L/min. The drug collected on the cascade impactor plates were assayed by the HPLC, and a drug mass balance was performed for each Diskhaler and multi-dose cascade impactor experiment consisting of determining the amount of drug left in the blister, the amount of drug remaining in the device (Diskhaler only), the non-respirable amount of the dose retained on the silicone rubber mouth piece adaptor, glass throat, glass distal pharynx and pre-separator, all combined into one sample, and the respirable dose, i.e. Stage 2 through filter impactor plates for airflow rates of 30 and 60 L/min and Stages 1 through filter impactor plates for 90 L/min experiments.

TABLE 5

Cascade Impactor Experiments (90 L/min)

| Inhaler Device | Pre-separator (%) | Blister (%) | Respirable Dose (%) | Device (%) | Mass Balance (%) |
|---|---|---|---|---|---|
| Diskhaler | 72.7 | 6.6 | 2.9 | 22.1 | 104.3 |
| Diskhaler | 60.2 | 10.1 | 2.4 | 13.3 | 86.0 |
| Multi-dose | 65.8 | 3.9 | 3.8 | 26.5 *a | 100.0 |
| Multi-dose | 73.3 | 3.8 | 3.6 | 19.3 *a | 100.0 |
| Multi-dose *b | 78.7 | 2.8 | 4.6 | 13.9 *a | 100.0 |
| Multi-dose *c | 55.9 | 5.0 | 1.2 | 37.9 *a | 100.0 |

*a Multi-dose device was not washed; as solvents would attack SLA components. Multi-dose device retention percentage is obtained by difference.
*b oven dried drug for 80 minutes
*c oven dried drug for 20 hours The following conclusions are derived from the emitted dose and cascade impactor experiments. The low respirable dose values achieved in the cascade impactor experiments were due to agglomerated drug particles, which could not be separated, even at the highest airflow rate tested. It is our opinion that agglomeration of the drug particles is a consequence of static charge build up during the mechanical milling process used for particles size reduction and that this situation is further compounded by subsequent moisture absorption of the particles. A micronization method that produces less static charge or a less hygroscopic, fully hydrated crystalline form of DHEA-S (i.e. dihydrate form) should provide a freer flowing powder with diminished potential for agglomeration.

Example 2

Spray Drying of Anhydrous DHEA Sulfate & Determination of Respirable Dose (1) Micronization of the Drug 1.5 g of anhydrous DHEA sulfate were dissolved to 100 ml of 50% ethanol:water to produce a 1.5% solution. The solution was spray-dried with a B-191 Mini Spray-Drier (Buchi, Flawil, Switzerland) with an inlet temperature of 55° C., outlet temperature of 40° C., at 100% aspirator, at 10% pump, nitrogen flow at 40 mbar and spray flow at 600 units. The spray-dried product was suspended in hexane and Span85 surfactant added to reduce agglomeration. The dispersions were sonicated with cooling for 3-5 minutes for complete dispersion and the dispersed solutions tested on a Malvern Mastersizer X with a Small Volume Sampler (SVS) attachment.

The two batches of spray dried material were found to have mean particle sizes of 5.07±0.70 μm and 6.66±0.91 μm. Visual examination by light microscope of the dispersions of each batch confirmed that spray drying produced small respirable size particles. The mean particle size was 2.4 μm and 2.0 μm for each batch, respectively. This demonstrates that DHEA-S can be spray dried to a particle size suitable for inhalation.

(2) Respirable Dose Studies

The cascade impactor experiments were conducted as described in Example 1. Four cascade impactor experiments were done, three with a IDL multi-dose device and one with a Diskhaler, all at 90 L/min. The results of the cascade impactor experiments are presented in Table 6 below.

TABLE 6

Cascade Impactor Results with Spray-Dried Drug Product

| Device | Diskhaler | Multi-dose | Multi-dose | Multi-dose |
|---|---|---|---|---|
| Number of Blisters | 3 | 3 | 4 | 4 |
| Drug per Blister (mg) | 38.2 | 36.7 | 49.4 | 50.7 |
| Preseparator (%) | 56.8 | 71.9 | 78.3 | 85.8 |
| Device (%) | 11.2 | 7.9 | 8.9 | 7.6 |
| Blisters (%) | 29.0 | 6.4 | 8.2 | 4.8 |
| Respirable Dose (%) | 5.6 | 7.8 | 5.3 | 2.6 |
| Mass Balance Recovery (%) | 102.7 | 94.0 | 103.3 | 98.1 |

The spray-dried anhydrous material in these experiments produced a two-fold increase in the respirable dose compared to micronized anhydrous DHEA-S. While it does appear that increased respirable doses were obtained with spray drying as compared to jet-milling, the % respirable dose was still low. This was due to agglomeration likely the result of moisture absorption of the anhydrous form.

Example 3

Air Jet Milling of DHEA-S Dihydrate (DHEA-S.2H$_2$O) & Determination of Respirable Dose (1) Recrystallization of DHEA-S dihydrate. Anhydrous DHEA-S is dissolved in a boiling mixture of 90% ethanol/water. This solution is rapidly chilled in a dry ice/methanol bath to recrystallize the DHEA-S. The crystals are filtered, washed twice with cold ethanol, than placed in a vacuum desiccator at room temperature for a total of 36 h. During the drying process, the material is periodically mixed with a spatula to break large agglomerates. After drying, the material is passed through a 500 µm sieve.

(2) Micronization and physiochecmical testing. DHEA-S dihydrate is micronized with nitrogen gas in a jet mill at a venturi pressure of 40 PSI, a mill pressure of 80 PSI, feed setting of 25 and a product feed rate of about 120 to 175 g/hour. Surface area is determined using five point BET analyses are performed with nitrogen as the adsorbing gas ($P/P_o$=0.05 to 0.30) using a Micromeritics TriStar surface area analyzer. Particle size distributions are measured by laser diffraction using a Micromeritics Saturn Digisizer where the particles are suspended in mineral oil with sodium dioctyl sodium sulfosuccinate as a dispersing agent. Drug substance water content is measured by Karl Fischer titration (Schott Titroline KF). Pure water is used as the standard and all relative standard deviations for triplicates are less than 1%. Powder is added directly to the titration media. The physicochemical properties of DHEA-S.dihydrate before and after micronization are summarized in Table 7.

TABLE 7

Physicochemical properties of DHEA-S - dihydrate before and after micronization.

| Property | Bulk | Micronized |
|---|---|---|
| Particle size ($D_{50\%}$) | 31 microns | 3.7 microns |
| Surface area ($m^2/g$) | Not measured | 4.9 |
| Water (% w/w) | 8.5 | 8.4 |
| Impurities | No significant peaks | No significant peaks |

The only significant change measured is in the particle size. There is no significant loss of water or increase in impurities. The surface area of the micronized material is in agreement with an irregularly shaped particle having a median size of 3 to 4 microns. The micronization successfully reduces the particle size to a range suitable for inhalation with no measured changes in the solid-state chemistry.

(3) Aerosolization of DHEA-S.dihydrate. The single-dose Acu-Breathe device is used for evaluating DHEA-S.dihydrate. Approximately 10 mg of neat DHEA-S.dihydrate powder is filled and sealed into foil blisters. These blisters are actuated into the Andersen 8-stage cascade impactor at flow rates ranging from 30 to 75 L/min with a glass twin-impinger throat. Stages 1-5 of the Andersen impactor are rinsed together to obtain an estimate of the fine particle fraction. Pooling the drug collected from multiple stages into one assay make the method much more sensitive. The results for this series of experiments is shown in FIG. 1.

At all flow rates, the dihydrate yields a higher fine particle fraction than the virtually anhydrous material. Since the dihydrate powder is aerosolized using the single-dose inhaler, it is very reasonable to conclude that its aerosol properties are significantly better than the virtually anhydrous material. Higher crystallinity and stable moisture content are the most likely factors contributing the dihydrate's superior aerosol properties. This unique feature of DHEA-S.dihydrate has not been reported in any previous literature.

While the improvement in DHEA-S's aerosol performance with the dihydrate form is significant, neat drug substance may not be the optimal formulation. Using a carrier with a larger particle size typically improves the aerosol properties of micronized drug substances.

Example 4

Anhydrous DHEA-S and DHEA-S Dihydrate Stability with and without Lactose

The initial purity (Time=0) was determined for anhydrous DHEA and for DHEA-S dihydrate by high pressure liquid chromatography (HPLC). Both forms of DHEA-S were then either blended with lactose at a ratio of 50:50, or used as a neat powder and placed in open glass vials, and held at 50° C. for up to 4 weeks. These conditions were used to stress the formulation in order to predict its long-term stability results. Control vials containing only DHEA-S (anhydrous or dihydrate) were sealed and held 25° C. for up to 4 weeks. Samples were taken and analyzed by HPLC also at 0, 1, 2, and 4 weeks to determine the amount of degradation, as determined by formation of DHEA.

After one week, virtually anhydrous DHEA-S blended with lactose (50% w/w, nominally) stored at 50° C. in sealed glass vials acquires a brown tinge that is darker for the lactose blend. This color change is accompanied by a significant change in the chromatogram as shown in FIG. 1. The primary degradant is dehydroepiandrosterone or DHEA. Qualitatively from FIG. 2, the amount of DHEA in the blend is higher than the other two samples. To quantitatively estimate the % DHEA in the samples, the area for the DHEA peak is divided by the total area for the DHEA-S and DHEA peaks (see Table 8 for results). The higher rate of decomposition for the blend indicates a specific interaction between lactose and the virtually anhydrous DHEA-S. In parallel with the increase in DHEA, the brown color of the powders on accelerated storage increased over time. The materials on accelerated storage become more cohesive with time as evidenced by clumping during sample weighing for chemical analysis. Based on these results, it is not possible to formulate virtually anhydrous DHEA-S with lactose. This is a considerable disadvantage since lactose is the most commonly used inhalation excipient for dry powder formulations. Continuing with the virtually anhydrous form would mean limiting formulations to neat powder or undertaking more comprehensive safety studies to use a novel excipient.

TABLE 8

DHEA % formed from Anhydrous DHEA-S at 50° C.

| Formulation | Time(Weeks) | 1 | 2 | 4 |
|---|---|---|---|---|
| Control | 2.774 | | | |
| DHEA-S. Alone | | 2.694 | 2.370 | 2.666 |
| DHEA-S + Lactose (50:50) | | 9.817 | 14.954 | 20.171 |
| | | 24.085 | 30.026 | 38.201 |

Figure 2:
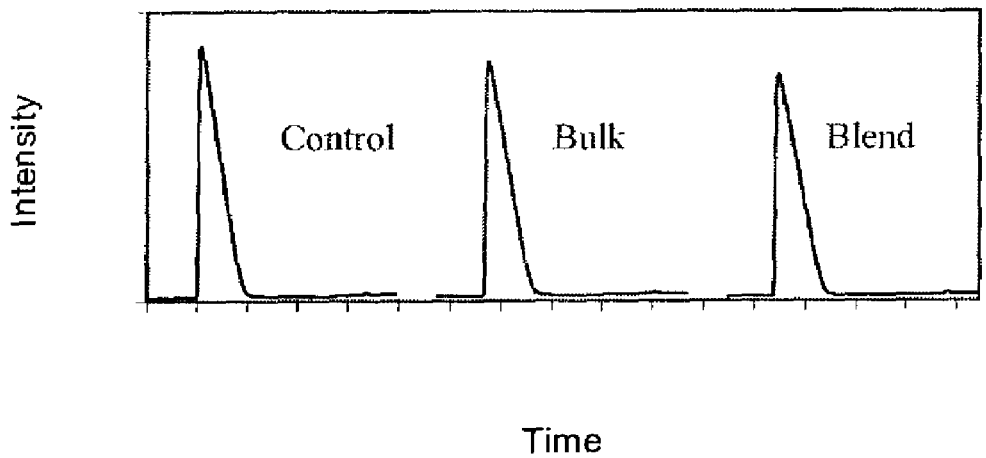
Figure 3:
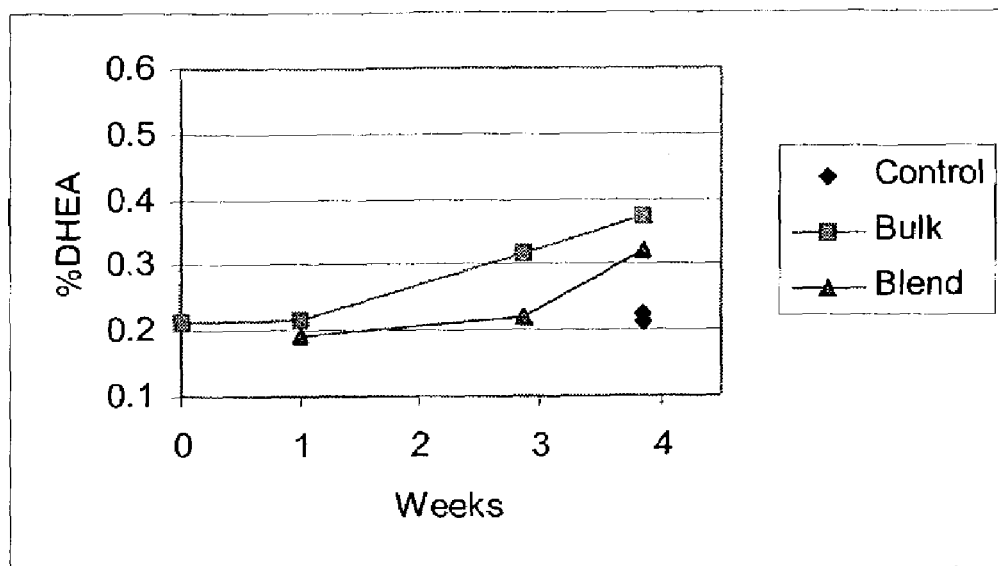

In contrast to FIG. 2, there is virtually no DHEA generated after storage for 1 week at 50° C. (see FIG. 3). Furthermore, the materials show no change in color. The moisture content of DHEA-S.dihydrate remains virtually unchanged after one week at 50° C. The water content after accelerated storage is 8.66% versus a starting value of 8.8%. The % DHEA measured during the course of this stability program is shown in Table 9.

TABLE 9

Percent DHEA formed from DHEA-S Dihydrate at 50° C.

| Formulation | Time (Weeks) | 1 | 3 | 4 |
|---|---|---|---|---|
| Control | 0.213 | | | 0.218 |
| DHEA-S alone | | 0.216 | 0.317 | 0.374 |
| DHEA-S:Lactose (50:50) | | 0.191 | 0.222 | 0.323 |

By comparing FIGS. 1 and 2 and Tables 8 and 9, one can see that the dihydrate form of DHEA-S is the more stable form for progression into further studies. The superior compatibility of DHEA-S.dihydrate with lactose over that of the virtually anhydrous material has not been reported in the patent or research literature. The solubility of this substance is reported in the next section as a portion of the development work for a nebulizer solution.

Example 5

DHEA-S Dihydrate/Lacotse Blends, Determination of Respirable Dose & Stability (1) DHEA-S dihydrate/Lactose blend. Equal weights of DHEA-S and inhalation grade lactose (Foremost Aero Flo 95) are mixed by hand then passed through a 500 µm screen to prepare a pre-blend. The pre-blend is then placed in a BelArt Micro-Mill with the remaining lactose to yield a 10% w/w blend of DHEA-S. The blender is wired to a variable voltage source to regulate the impeller speed. The blender voltage is cycled through 30%, 40%, 45% and 30% of full voltage for 1, 3, 1.5, and 1.5 minutes, respectively. The content uniformity of the blend was determined by HPLC analysis. Table 10 shows the result of content uniformity samples for this blend. The target value is 10% w/w DHEA-S. The blend content is satisfactory for proximity to the target value and content uniformity.

TABLE 10

Content uniformity for a blend of DHEA-S - dihydrate with lactose.

| Sample | % DHEA-S, w/w |
|---|---|
| 1 | 10.2 |
| 2 | 9.7 |
| 3 | 9.9 |
| 4 | 9.3 |
| 5 | 9.4 |
| Mean | 9.7 |
| RSD | 3.6% |

(2) Aerosolization of DHEA-S.dihydrate/Lactose blend. Approximately 25 mg of this powder is filled and sealed in foil blisters and aerosolized using the single-dose device at 60 L/min. Two blisters are used for each test and the results for fine particle fraction (material on stages 1-5) are shown in Table 11.

TABLE 11

Fine particle fraction for lactose blend in two different experiments

| Test | Total powder weight in two blisters (mg) | DHEA-S collected Stages 1-5 (mg) | Fine particle fraction, % |
|---|---|---|---|
| 1 | 52.78 | 1.60 | 31 |
| 2 | 57.09 | 1.62 | 29 |

The aerosol results for this preliminary powder blend are satisfactory for a respiratory drug delivery system. Higher fine particle fractions are possible with optimization of the powder blend and blister/device configuration. The entire particle size distribution of Test 2 is shown in Table 12.

TABLE 12

Particle size distribution of aerosolized DHEA-S dihydrate/Lactose Blend

| Size (µm) | 6.18 | 9.98 | 3.23 | 2.27 | 1.44 | 0.76 | 0.48 | 0.27 |
|---|---|---|---|---|---|---|---|---|
| % Particles Under | 100 | 87.55 | 67.79 | 29.87 | 10.70 | 2.57 | 1.82 | 0.90 |

This median diameter for DHEA-S for this aerosol is ~2.5 µm. This diameter is smaller than the median diameter measured for micronized DHEA-S.dihydrate by laser diffraction. Irregularly shaped particles can behave aerodynamically as smaller particles since their longest dimension tends to align with the air flow field. Therefore, it is common to see a difference between the two methods. Diffraction measurements are a quality control test for the input material while cascade impaction is a quality control test for the finished product.

(3) Stability of DHEA-S Dihydrate/Lactose Blend. This lactose formulation is also placed on an accelerated stability program at 50° C. The results for DHEA-S content are in Table 13. The control is the blend stored at room temperature.

TABLE 13

Stressed stability data on DHEA-S · dihydrate/lactose blend at 50° C.

| Time (weeks) | % DHEA-S w/w for control condition | % DHEA-S w/w for stressed condition |
|---|---|---|
| 0 | 9.7 | 9.7 |
| 1 | 9.6 | 9.6 |
| 1.86 | 9.5 | 9.7 |
| 3 | 10 | 9.9 |

There is no trend in the DHEA-S content over time for either condition and all the results are within the range of samples collected for content uniformity testing (see Table 13). Furthermore, there are no color changes or irregularities observed in the chromatograms. The blend appears to be chemically stable.

Example 6

Nebulizer Formulation of DHEA-S

Solubility of DHEA-S. An excess of DHEA-S dihydrate, prepared according to "Recrystallization of DHEA-S.Dihydrate (Example 4)", is added to the solvent medium and allowed to equilibrate for at least 14 hours with some periodic shaking. The suspensions are then filtered through a 0.2 micron syringe filter and immediately diluted for HPLC analysis. To prepare refrigerated samples, the syringes and filters are stored in the refrigerator for at least one hour before use.

Figure 4:
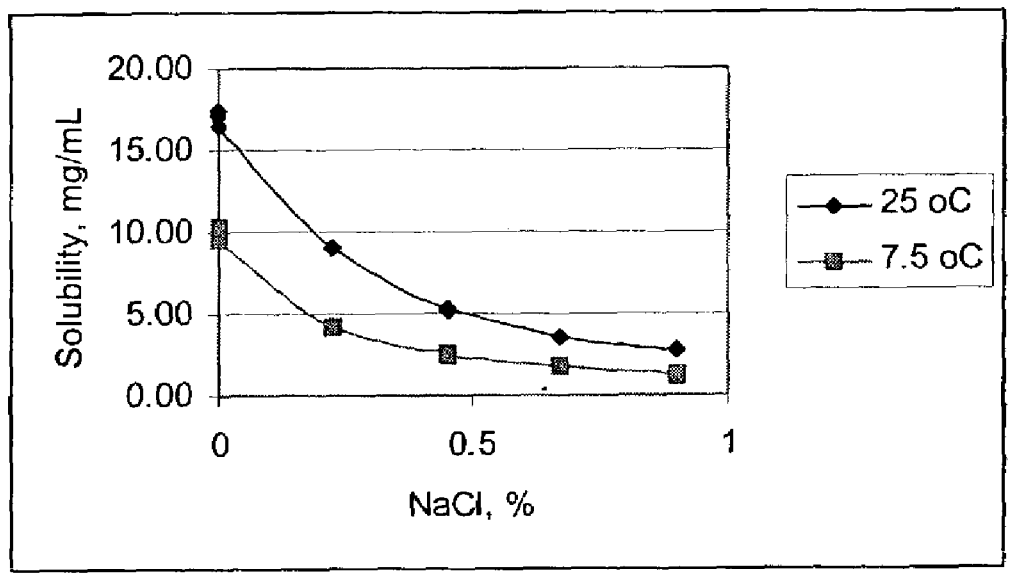

Inhalation of pure water can produce a cough stimulus. Therefore, it is important to add halide ions to a nebulizer formulation with NaCl being the most commonly used salt. Since DHEA-S is a sodium salt, NaCl could decrease solubility due to the common ion effect. The solubility of DHEA-S at room temperature (24-26° C.) and refrigerated (7-8° C.) as a function of NaCl concentration is shown in FIG. 4.

DHEA-S's solubility decrease with NaCl concentration. Lowering the storage temperature decrease the solubility at all NaCl concentrations. The temperature effect is weaker at high NaCl concentrations. For triplicates, the solubility at ~25° C. and 0% NaCl range from 16.5-17.4 mg/mL with a relative standard deviation of 2.7%. At 0.9% NaCl refrigerated, the range for triplicates is 1.1-1.3 mg/mL with a relative standard deviation of 8.3%.

The equilibrium between DHEA-S in the solid and solution states is:

$$NaDHEA\text{-}S_{solid} \leftrightarrows DHEA\text{-}S^- + Na^+$$

$$K = [DHEA\text{-}S^-][Na^+]/[NaDHEA\text{-}S]_{solid}$$

Since the concentration of DHEA-S in the solid is constant (i.e., physically stable dihydrate), the equilibrium expression is simplified:

$$Ksp = [DHEA\text{-}S^-][Na^+]$$

Figure 5:
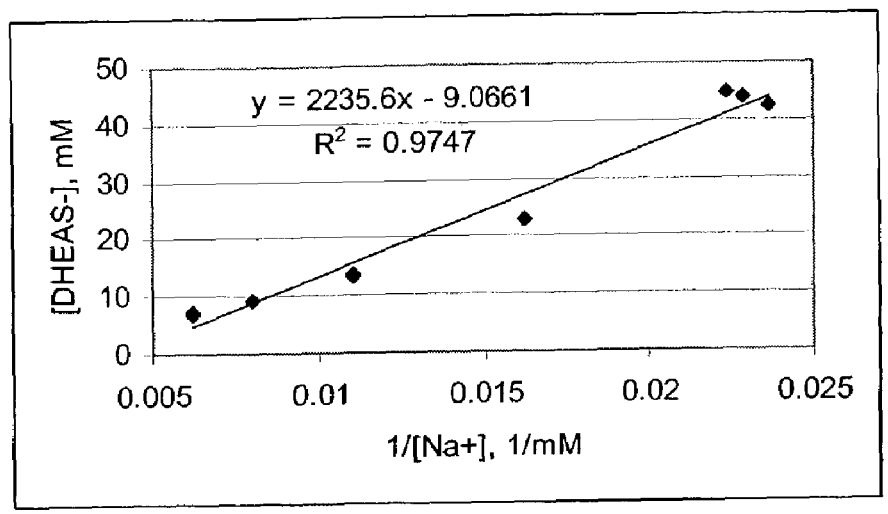
Figure 6:
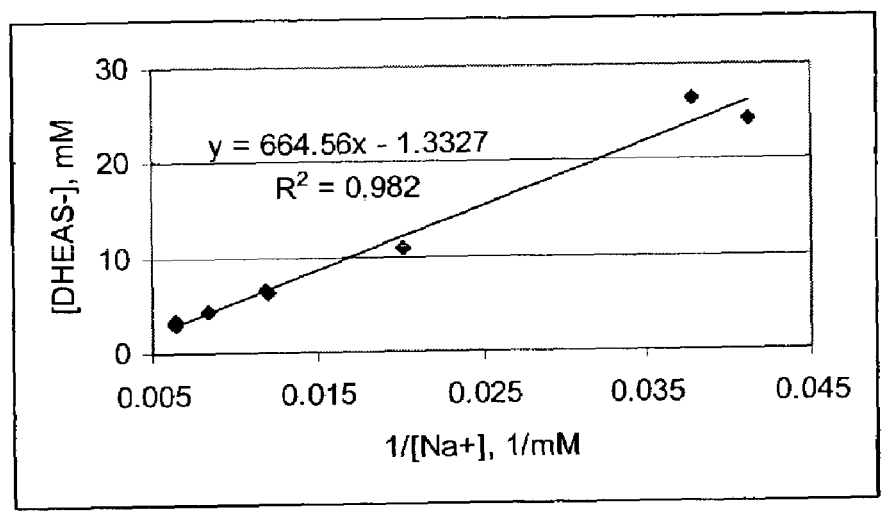

Based on this presumption, a plot of DHEA-S solubility versus the reciprocal of the total sodium cation concentration is linear with a slope equal to Ksp. This is shown in FIGS. 5 and 6 for equilibrium at room temperature and refrigerated, respectively.

Based on the correlation coefficients, the model is a reasonable fit to the data at both room and refrigerated temperatures where the equilibrium constants were 2236 and 665 mM$^2$, respectively. To maximize solubility, the NaCl level needs to be as low as possible. The minimum halide ion content for a nebulizer solution should be 20 mM or 0.12% NaCl.

To estimate a DHEA-S concentration for the solution, a 10° C. temperature drop in the nebulizer during use is assumed (i.e., 15° C.). Interpolating between the equilibrium constants versus the reciprocal of absolute temperature, the Ksp at 15° C. would be ~1316 mM$^2$. Each mole of DHEA-S contributes a mole of sodium cation to the solution, therefore:

$$Ksp = [DHEA\text{-}S^-][Na^+]$$
$$= [DHEA\text{-}S^-][Na^+ + DHEA\text{-}S^-]$$
$$= [DHEA\text{-}S^-]^2 + [Na^+][DHEA\text{-}S^-]$$

which is solve for [DHEA-S$^-$] using the quadratic formula. The solution for 20 mM Na$^+$ with a Ksp of 1316 mM$^2$ is 27.5 mM DHEA-S$^-$ or 10.7 mg/mL. Therefore a 10 mg/mL DHEA-S solution in 0.12% NaCl is selected as a good candidate formulation to progress into additional testing. The estimate for this formula does not account for any concentration effects due to water evaporation from the nebulizer.

Figure 7:
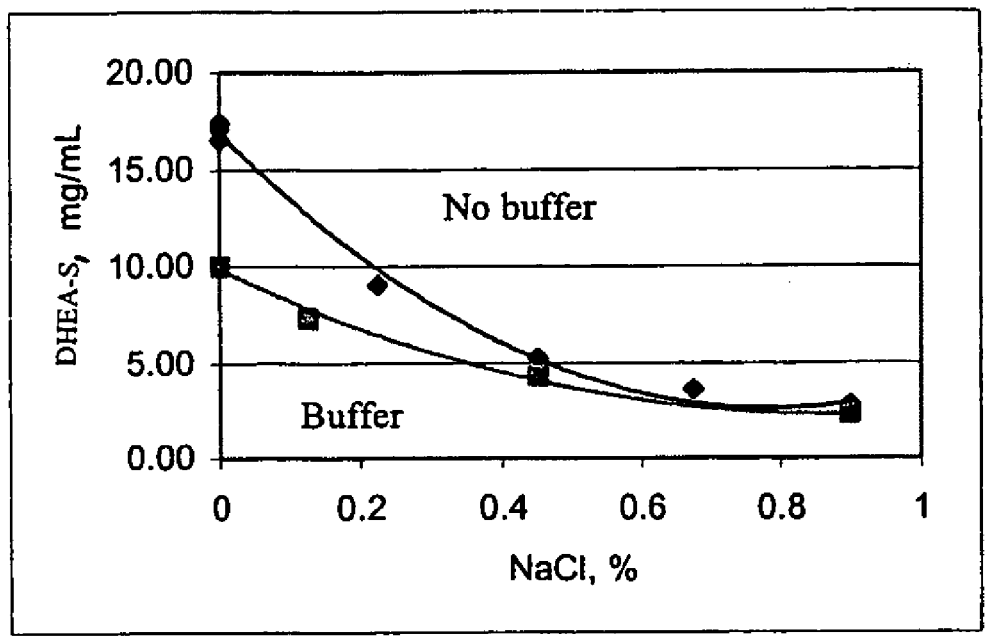

The pH of a 1 0 mg/mL DHEA-S solution with 0.12% NaCl range from 4.7 to 5.6. While this would be an acceptable pH level for an inhalation formulation, the effect of using a 20 mM phosphate buffer is evaluated. The solubility results at room temperature for buffered and unbuffered solutions are shown in FIG. 7.

Figure 8:
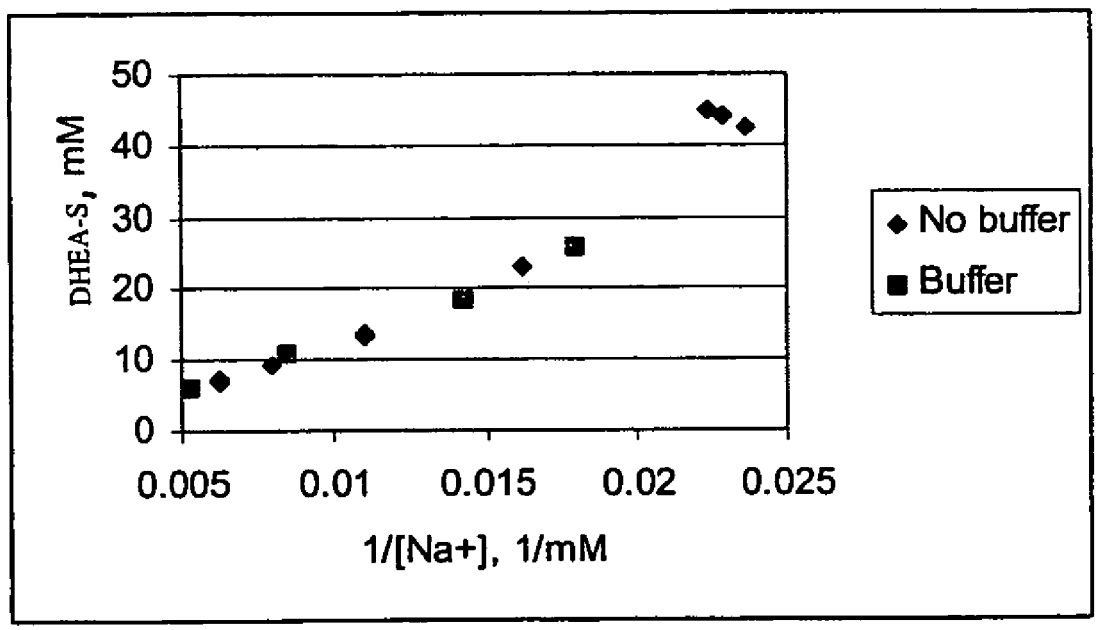

The presence of buffer in the formulation suppress the solubility, especially at low NaCl levels. As shown in FIG. 8, the solublity data for the buffered solution falls on the same equilibrium line as for the unbuffered solution. The decrease in solubility with the buffer is due to the additional sodium cation content.

Maximizing solubility is an important goal and buffering the formulation reduces solubility. Furthermore, Ishihora and Sugimoto ((1979) *Drug Dev. Indust. Pharm.* 5(3) 263-275) did not show a significant improvement in NaDHEA-S stability at neutral pH.

Figure 9:
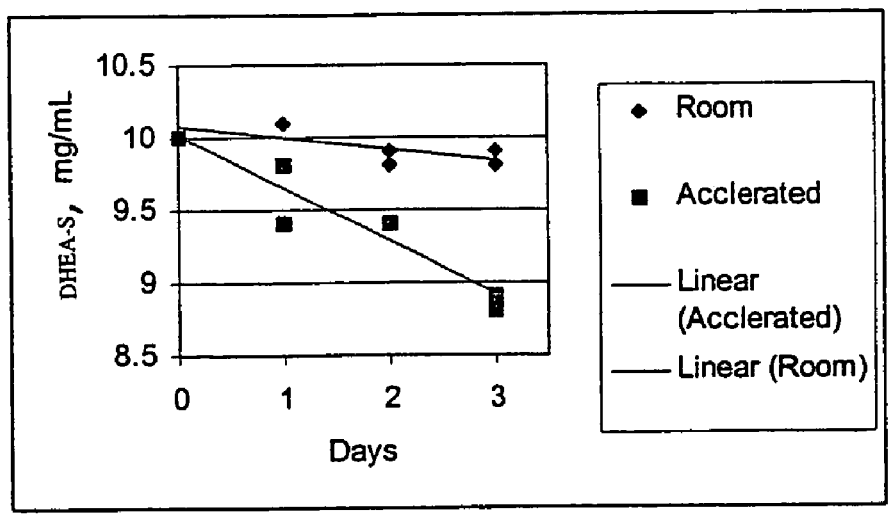
Figure 10:
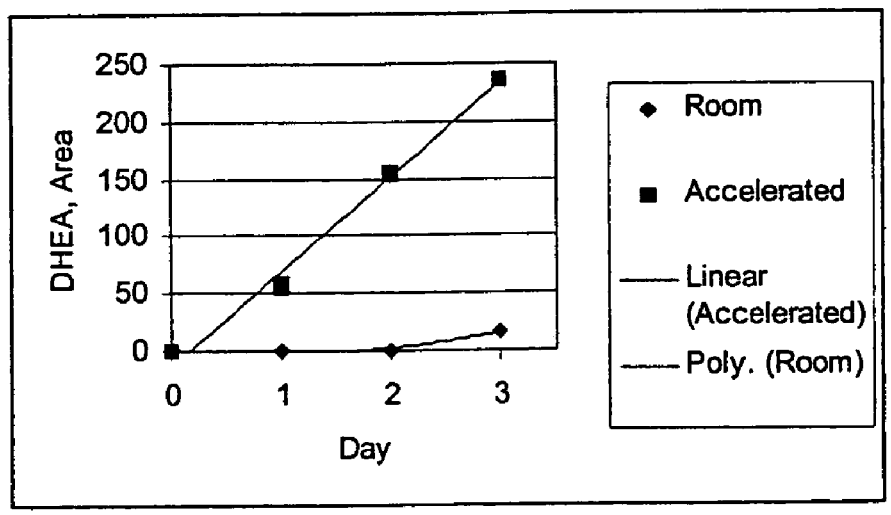

Stability Studies. A 10 mg/mL DHEA-S formulation is prepared in 0.12% NaCl for a shortterm solution stability program. Aliquots of this solution are filled into clear glass vials and stored at room temperature (24-26° C.) and at 40° C. The samples are checked daily for DHEA-S content, DHEA content, and appearance. For each time point, duplicate samples are withdrawn and diluted from each vial. The DHEA-S content over the length of this study is shown in FIGS. 9 and 10.

At the accelerated condition, the solution show a faster decomposition rate and became cloudy after two days of storage. The solution stored at room temperature is more stable and a slight precipitate is observed on the third day. The study is stopped on day three. DHEA-S decomposition is accompanied by an increase in DHEA content as shown in FIG. 10.

Since DHEA is insoluble in water, it only takes a small quantity in the formulation to create a cloudy solution (accelerated storage) or a crystalline precipitate (room storage). This explains why earlier visual evaluations of DHEA-S solubility severely underestimate the compound's solubility: small quantities of DHEA would lead the experimenter to conclude the solubility limit of DHEA-S had been exceeded. While this is not a promising commercial formulation, the solution should easily be stable for the day of reconstitution in a clinical trial. The following section describes the aerosol properties of this formulation.

Figure 11:
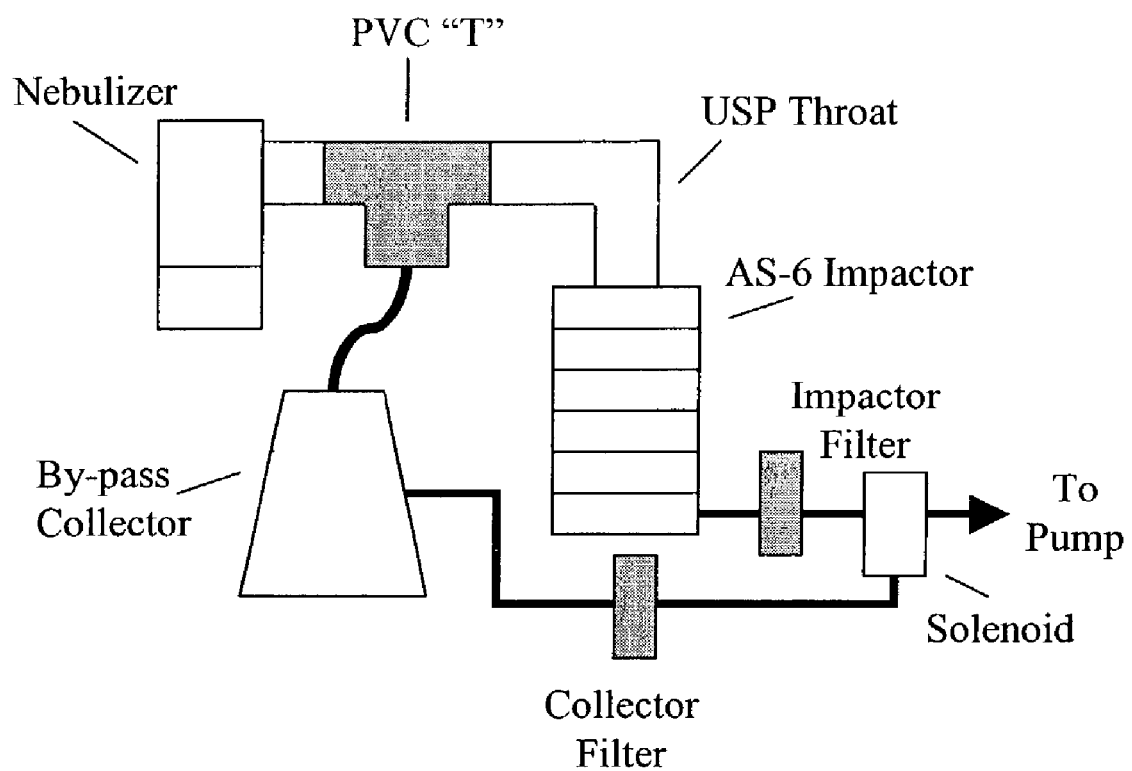

Nebulizer Studies. DHEA-S solutions are nebulized using a Pari ProNeb Ultra compressor and LC Plus nebulizer. The schematic for the experiment set-up is shown in FIG. 11. The nebulizer is filled with 5 mL of solution and nebulization is continued until the output became visually insignificant (4½ to 5 min.). Nebulizer solutions are tested using a California Instruments AS-6 6-stage impactor with a USP throat. The impactor is run at 30 L/min for 8 seconds to collect a sample following one minute of nebulization time. At all other times during the experiment, the aerosol is drawn through the bypass collector at approximately 33 L/min. The collection apparatus, nebulizer, and impactor are rinsed with mobile phase and assayed by HPLC. 5 mL of DHEA-S in 0.12% NaCl is used in the nebulizer. This volume is selected as the practical upper limit for use in a clinical study. The results for the first 5 nebulization experiments are shown below:

TABLE 14

Results for nebulization studies with DHEA-S

| Solution-Nebulizer # | Left in Nebulizer, mg | Deposited in Collector, mg | Deposited in Impactor, mg | Total, mg |
|---|---|---|---|---|
| 10 mg/mL-1 | 17.9* | 16.3 | 0.38 | 34.6 |
| 10 mg/mL-2 | 31.2 | 17.2 | 0.48 | 49.0 |
| 7.5 mg/mL-1 | 19.3 | 16.3 | 0.35 | 36.0 |
| 7.5 mg/mL-1 | 21.7 | 15.4 | 0.30 | 37.4 |
| 5.0 mg/mL-1 | 14.4 | 10.6 | 0.21 | 25.2 |

*Only assayed liquid poured from nebulizer; did not weigh before and after aerosolization or rinse entire unit Nebulizer #1 runs to dryness in about 5 minutes while Nebulizer #2 takes slightly less than 4.5 minutes. In each case, the liquid volume remaining in the nebulizer is approximately 2 mL. This liquid is cloudy initially after removal from the nebulizer then clears within 3-5 minutes. Even after this time, the 10 mg/mL solutions appear to have a small amount of coarse precipitate in them. Fine air bubbles in the liquid appear to cause the initial cloudiness. DHEA-S appears to be surface active (i.e., promoting foam) and this stabilizes air bubbles within the liquid. The precipitate in 10 mg/mL solutions indicates that the drug substance's solubility is exceeded in the nebulizer environment. Therefore, the additional nebulization experiments in Table 15 are run at lower concentrations.

Table 15 presents additional data of "dose" linearity versus solution concentration.

TABLE 15

Results from additional nebulizer experiments with DHEA-S.

| Solution-Nebulizer # | Left in Nebulizer, mg | Deposited in Collector, mg | Deposited in Impactor, mg | Total, mg |
|---|---|---|---|---|
| 6.25 mg/mL-2 | 17.8 | 12.1 | 0.24 | 30.1 |
| 7.5 mg/mL-3 | 21.2 | 13.8 | 0.33 | 35.3 |

Figure 12:
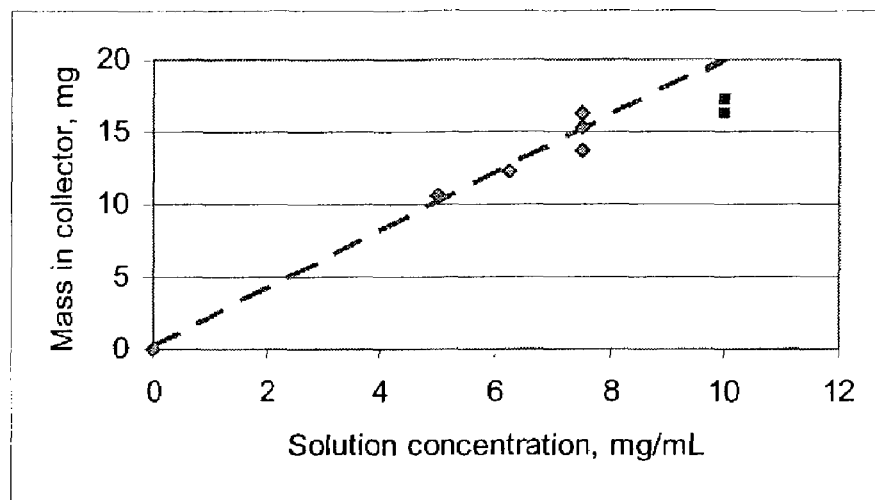

Nebulizer #3 takes slightly less than 4.5 minutes to reach dryness. The mass in the bypass collector is plotted versus the initial solution concentration in FIG. 12.

Semi-quantitatively, there is good linearity from 0 to 7.5 mg/mL then the amount collected appears to start leveling-off. While the solubility reduction by cooling is included in the calculation of the 10 mg/mL solution, any concentration effects on drug and NaCl content were neglected. Therefore, it is possible for a precipitate to form via supersaturation of the nebulizer liquid. The data in FIG. 12 and the observation of some particulates in the 10 mg/mL solution following nebulization indicate that the highest solution concentration for a proof of concept clinical trial formulation is approximately 7.5 mg/mL.

Figure 13:
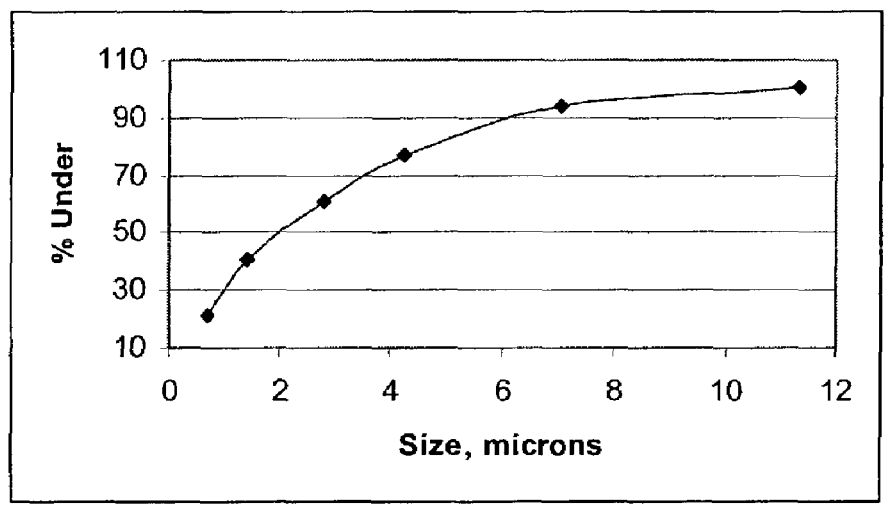

An aerosol sample is drawn into a cascade impactor for particle size analysis. There is no detectable trend in particle size distribution with solution concentration or nebulizer number. The average particle size distribution for all nebulization experiments is shown in FIG. 13. The aerosol particle size measurements are in agreement with published/advertised results for this nebulizer (i.e., median diameter ~2 μm).

While the in vitro experiments demonstrate that a nebulizer formulation can deliver respirable DHEA-S aerosols, the formulation is unstable and takes 4-5 minutes of continuous nebulization. Therefore, a stable DPI formulation has significant advantages. DHEA-S.dihydrate is identified as the most stable solid state for a DPI formulation. The anhydrous form is also suitable for administration with the nebulizer if its stability is maintained by eliminating its contact with water prior to nebulization.

An optimal nebulizer formulation is 7.5 mg/mL of DHEA-S in 0.12% NaCl for clinical trials for DHEA-S. The pH of the formulation is acceptable without a buffer system. The aqueous solubility of DHEA-S is maximized by minimizing the sodium cation concentration. Minimal sodium chloride levels without buffer achieve this goal. This is the highest drug concentration with 20 mM of Cl$^-$ that will not precipitate during nebulization. This formulation is stable for at least one day at room temperature.

Although the invention has been described with reference to the presently preferred embodiments, it should be understood that various modifications can be made without departing from the spirit of the invention.

All publications, patents, and patent applications, and web sites are herein incorporated by reference in their entirety to the same extent as if each individual publication, patent, or patent application, was specifically and individually indicated to be incorporated by reference in its entirety.

What is claimed is:

1. A pharmaceutical composition comprising an agent, wherein the agent comprises a compound as described by chemical formula (I), (II), (III), (IV) or (V), or a pharmaceutically or veterinarily acceptable salt thereof, in an anhydrous form thereof;

wherein the broken line represents a single or a double bond;

wherein R is hydrogen or a halogen; the H at position 5 is present in the alpha or beta configuration or the compound of formula (I) comprises either isomer or a racemic mixture of both configurations;

and $R_1$ is hydrogen or a multivalent inorganic or organic dicarboxylate acid covalent bound to the compound of chemical formula (I);

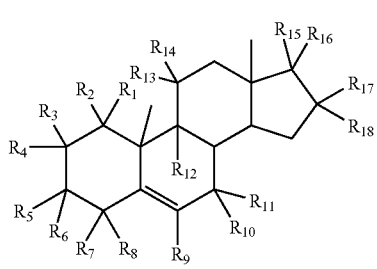
(III)

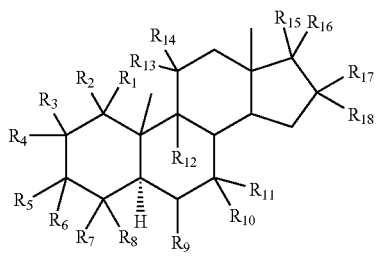
(IV)

wherein $R_1$, $R_2$, $R_3$, $R_4$, $R_6$, $R_7$, $R_8$, $R_9$, $R_{10}$, $R_{11}$, $R_{12}$, $R_{13}$, $R_{14}$ and $R_{19}$ are independently H, OH, halogen, $C_{1-10}$ alkyl or $C_{1-10}$ alkoxy; $R_5$ is H, OH, halogen, $C_{1-10}$ alkyl, $C_{1-10}$ alkoxy or $OSO_2R_{20}$; $R_{15}$ is (1) H, halogen, $C_{1-10}$ alkyl or $C_{1-10}$ alkoxy when $R_{16}$ is $C(O)OR_{21}$ or (2) H, halogen, OH or $C_{1-10}$ alkyl when $R_{16}$ is H, halogen, OH or $C_{1-10}$ alkyl or (3) H, halogen, $C_{1-10}$ alkyl, $C_{1-10}$ alkenyl, $C_{1-10}$ alkynyl, formyl, $C_{1-10}$ alkanoyl or epoxy when $R_{16}$ is OH; or $R_{15}$ and $R_{16}$ taken together are =O; $R_{17}$ and $R_{18}$ are independently (1) H, OH, halogen, $C_{1-10}$ alkyl or $C_{1-10}$ alkoxy when $R_{16}$ is H, OH, halogen, $C_{1-10}$ alkyl or —$C(O)OR_{21}$ or (2) H, $(C_{1-10}\text{ alkyl})_n$ amino, $(C_{1-10}\text{ alkyl})_n$ amino-$C_{1-10}$ alkyl, $C_{1-10}$ alkoxy, hydroxy-$C_{1-10}$ alkyl, $C_{1-10}$ alkoxy-$C_{1-10}$ alkyl, $(\text{halogen})_m$-$C_{1-10}$ alkyl, $C_{1-10}$ alkanoyl, formyl, $C_{1-10}$ carbalkoxy or $C_{1-10}$ alkanoyloxy when $R_{15}$ and $R_{16}$ taken together are =O; or $R_{17}$ and $R_{18}$ taken together are =O or taken together with the carbon to which they are attached form a 3-6 member ring containing 0 or 1 oxygen atoms; or $R_{15}$ and $R_{17}$ taken together with the carbons to which they are attached form an epoxide ring; [$R_{20}$ is OH, pharmaceutically acceptable ester or pharmaceutically acceptable ether; $R_{21}$ is H, $(\text{halogen})_m$ -$C_{1-10}$ alkyl or $C_{1-10}$ alkyl]; n is 0, 1 or 2; and m is 1, 2 or 3, with the proviso that (a) $R_3$ is not H, OH or halogen when $R_1$, $R_2$, $R_4$, $R_6$, $R_7$, $R_9$, $R_{10}$, $R_{12}$, $R_{13}$, $R_{14}$, $R_{17}$ and $R_{19}$ are H and $R_5$ is OH or $C_{1-10}$ alkoxy and $R_8$ is H, OH or halogen and $R_{11}$ is H or OH and $R_{18}$ is H, halogen or methyl and $R_{15}$ is H and $R_{16}$ is OH; (b) $R_3$ is not H, OH or halogen when $R_1$, $R_2$, $R_4$, $R_6$, $R_7$, $R_9$, $R_{10}$, $R_{12}$, $R_{13}$, and $R_{14}$ [and $R_{19}$ ] are H and $R_5$ is OH or $C_{1-10}$ alkoxy and $R_8$ is H, OH or halogen and $R_{11}$ is H or OH and $R_{18}$ is H, halogen or methyl and $R_{15}$ and $R_{16}$ taken together are =O; (c) $R_5$ is not H, halogen, $C_{1-10}$ alkoxy or $OSO_2R_{20}$ when $R_1$, $R_2$, $R_3$, $R_4$, $R_6$, $R_7$, $R_8$, $R_9$, $R_{10}$, $R_{12}$, $R_{13}$, $R_{14}$ and $R_{17}$ are H and $R_{11}$ is H, halogen, OH or $C_{1-10}$ alkoxy and $R_{18}$ is H or halogen and $R_{15}$ and $R_{16}$ taken together are =O; and (d) $R_5$ is not H, halogen, $C_{1-10}$ alkoxy or $OSO_2R_{20}$ when $R_1$, $R_2$, $R_3$, $R_4$, $R_6$, $R_7$, $R_8$, $R_9$, $R_{10}$, $R_{12}$, $R_{13}$, $R_{14}$ and $R_{17}$ are H and $R_{11}$ is H, halogen, OH or $C_{1-10}$ alkoxy and $R_{18}$ is H or halogen and $R_{15}$ is H and $R_{16}$ is H, OH or halogen;

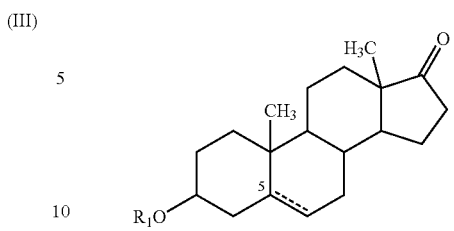
(V)

wherein R is A —CH(OH)—C(O)— and A is hydrogen or a $C_1$-$C_{22}$ alkyl or alkenyl group wherein the $C_1$-$C_{22}$ alkyl or alkenyl group is not subsitutued or substituted with one or more $C_1$-$C_4$ alkyl groups, phenyls, halogens or hydroxyl groups, said phenyl is not substituted or substituted with one or more halogen HO or $CH_3O$;

wherein said dry powder pharmaceutical composition is particles of respirable or inhalable size.

2. The pharmaceutical composition of claim 1, wherein the multivalent inorganic acid is $SO_2OM$, phosphate or carbonate, wherein M is selected from the group consisting of H, Na, sulphatide, and phosphatide wherein $R_2$ and $R_3$, which may be the same or different, are straight or branched ($C_1$-$C_{14}$) alkyl or glucuronide wherein the multivalent organic dicarboxylic acid is succinate, maleate, or fumarate.

3. The pharmaceutical composition of claim 1, wherein powder pharmaceutical composition further comprises a pharmaceutically or veterinarily acceptable excipient.

4. The pharmaceutical composition of claim 3, wherein said excipient is one selected from human protein, bovine serum albumin, gelatin, immunoglobulins, galactose, D-mannose, sorbose, trehalose, sucrose, cyclodextrins, raffinose, maltodextrins, dextrans, monosodium glutamate, glycine, alanine, arginine or histidine, tryptophan, tyrosine, leucine, phenylalanine, betaine, magnesium sulfate, magnesium stearate, glycerin, erythritol, glycerol, arabitol, xylitol, sorbitol, mannitol, propylene glycbl, polyethylene glycol, pluronics, surfactants, and a mixture thereof.

5. The pharmaceutical composition of claim 1, wherein the agent comprises a compound as described by chemical formula (II):

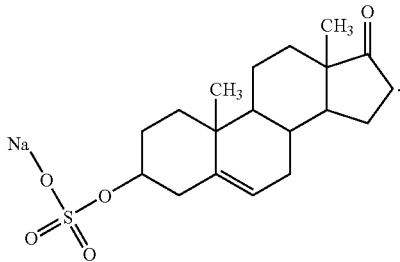

(II)

6. The pharmaceutical composition of claim 1, wherein said powder pharmaceutical composition is deliverable using a nebulizer, a dry powder inhaler, an insufflator, or an aerosol or spray generator.

7. The pharmaceutical composition of claim 1, wherein said powder pharmaceutical composition is produced by jet-milling.

8. The pharmaceutical composition of claim 1, wherein greater than 80% of the particles are about 0.1 μm to about 100 μm in diameter.

9. The pharmaceutical composition of claim 8, wherein greater than 80% of the particles are about 0.1 μm to about 50 μm.

10. The pharmaceutical composition of claim 9, wherein greater than 80% of the particles are about 0.1 μm to about 10 μm.

11. The pharmaceutical composition of claim 10, wherein greater than 90% of the particles are about 0.1 μm to about 5 μm.

12. The pharmaceutical composition of claim 1, further comprising a therapeutic agent selected from inhibitors of the adenosine $A_1$ receptor, inhibitors of the adenosine $A_{2b}$ receptor, inhibitors of the adenosine $A_3$ receptor, adenosine $A_{2a}$ receptor stimulating agents, anti-inflammatory agents, anti-bacterial agents, anti-sepsis agents, kidney activity maintenance or restoration agents, and agents for treatment of pulmonary vasoconstriction, inflammation, allergies, asthma, impeded respiration, respiratory distress syndrome, pain, cystic fibrosis (CF), pulmonary hypertension, pulmonary vasoconstriction, emphysema, chronic obstructive pulmonary disease (COPD), allergic rhinitis (AR), SARS, and lung cancer.

13. A sealed container comprising the composition of claim 1, wherein said sealed container is vacuum sealed.

14. A kit comprising the sealed container of claim 13 and a second sealed container containing a pharmaceutically acceptable propellant for the pharmaceutical composition.

15. The kit of claim 14, further comprising a nebulizer.

16. A method for treatment of asthma, comprising administering to a subject in need of such treatment a therapeutically effective amount of the powder pharmaceutical composition from the sealed container of claim 13.

17. A method for treatment of chronic obstructive pulmonary disease, comprising administering to a subject in need of such treatment a therapeutically effective amount of the powder pharmaceutical composition from the sealed container of claim 13.

18. A method of reducing or depleting adenosine in a subject's tissue, comprising administering to a subject in need of such treatment a therapeutically effective amount of the powder pharmaceutical composition from the sealed container of claim 13 to reduce or deplete adenosine levels in the subject's tissue.

19. The method of claim 18, wherein subject suffers from airway inflammation, allergy, asthma, impeded respiration, cystic fibrosis, Chronic Obstructive Pulmonary Diseases, allergic rhinitis, Acute Respiratory Distress Syndrome, microbial infection, SARS, pulmonary hypertension, lung inflammation, bronchitis, airway obstruction, or bronchoconstriction.

20. A method for treatment of a disorder or condition associated with high levels of, or sensitivity to, adenosine in a subject's tissue, comprising administering to a subject in need of such treatment a therapeutically effective amount of the powder pharmaceutical composition from the sealed container of claim 1 to reduce adenosine levels in the subject's tissue and prevent or treat the disorder.

21. The method of claim 20, wherein the disorder or condition is airway inflammation, allergy, asthma, impeded respiration, cystic fibrosis, Chronic Obstructive Pulmonary Diseases, allergic rhinitis, Acute Respiratory Distress Syndrome, microbial infection, SARS, pulmonary hypertension, lung inflammation, bronchitis, airway obstruction, or bronchoconstriction.

* * * * *